US012595476B2

(12) United States Patent
Duvall et al.

(10) Patent No.: US 12,595,476 B2
(45) Date of Patent: Apr. 7, 2026

(54) ASSEMBLY AND ERROR REDUCTION OF SYNTHETIC GENES FROM OLIGONUCLEOTIDES

(71) Applicant: ModernaTX, Inc., Cambridge, MA (US)

(72) Inventors: Marcus R. Duvall, Cambridge, MA (US); Kevin Smith, Franklin, MA (US); Robin Huang, Norwood, MA (US); Andrew Giessel, Somerville, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/982,135

(22) PCT Filed: Mar. 19, 2019

(86) PCT No.: PCT/US2019/022918
§ 371 (c)(1),
(2) Date: Sep. 18, 2020

(87) PCT Pub. No.: WO2019/183055
PCT Pub. Date: Sep. 26, 2019

(65) Prior Publication Data
US 2021/0163922 A1      Jun. 3, 2021

Related U.S. Application Data

(60) Provisional application No. 62/644,919, filed on Mar. 19, 2018.

(51) Int. Cl.
C12P 19/34       (2006.01)
C12N 15/10       (2006.01)
C12Q 1/6848      (2018.01)

(52) U.S. Cl.
CPC ..... *C12N 15/1031* (2013.01); *C12N 15/1027* (2013.01); *C12Q 1/6848* (2013.01)

(58) Field of Classification Search
USPC .......... 435/6.1, 6.11, 6.12, 91.1, 91.2, 287.1, 435/287.2; 436/94, 501; 536/23.1, 24.3, 536/24.33, 25.3
See application file for complete search history.

(56) References Cited

U.S. PATENT DOCUMENTS

| | | | | |
|---|---|---|---|---|
| 4,243,753 | A | * | 1/1981 | Regnier ................. C12M 27/00 |
| | | | | 435/26 |
| 4,921,802 | A | * | 5/1990 | Hall ......................... C12Q 1/70 |
| | | | | 536/23.6 |
| 5,219,727 | A | | 6/1993 | Wang et al. |
| 5,538,871 | A | | 7/1996 | Nuovo et al. |
| | | | | (Continued) |

OTHER PUBLICATIONS

"T7 endonuclease I" from New England BioLabs. Printed on Nov. 1, 2022.*

(Continued)

*Primary Examiner* — Frank W Lu
(74) *Attorney, Agent, or Firm* — Clark & Elbing LLP

(57) ABSTRACT

The present invention relates to a rapid, high-fidelity process to support synthesis of genes for in vitro transcription of modified messenger RNA. In this process, sequence errors resulting from amplification with oligonucleotides comprising inherent errors are significantly reduced.

27 Claims, 14 Drawing Sheets
Specification includes a Sequence Listing.

Method for reducing error-rate in assembled dsDNA fragments

(56) References Cited

U.S. PATENT DOCUMENTS

| | | | | |
|---|---|---|---|---|
| 5,556,773 | A | 9/1996 | Yourno | |
| 5,786,464 | A | 7/1998 | Seed | |
| 6,114,148 | A | 9/2000 | Seed et al. | |
| 2004/0219523 | A1* | 11/2004 | Stanton | C12Q 1/6825 |
| | | | | 435/6.14 |
| 2006/0134638 | A1* | 6/2006 | Mulligan | C12Q 1/6827 |
| | | | | 435/6.1 |
| 2006/0194214 | A1* | 8/2006 | Church | C12Q 1/6813 |
| | | | | 435/6.16 |
| 2007/0128649 | A1* | 6/2007 | Young | C12N 15/1093 |
| | | | | 977/924 |
| 2007/0269870 | A1 | 11/2007 | Church et al. | |
| 2009/0118484 | A1 | 5/2009 | Wang | |
| 2009/0324546 | A1 | 12/2009 | Notka et al. | |
| 2011/0172127 | A1 | 7/2011 | Jacobson et al. | |
| 2013/0295631 | A1* | 11/2013 | Zhao | C12N 9/1205 |
| | | | | 435/254.22 |
| 2017/0029881 | A1* | 2/2017 | Trau | C12Q 1/703 |
| 2019/0203283 | A1* | 7/2019 | Woodhouse | C12Q 1/6806 |
| 2020/0024654 | A1* | 1/2020 | Heron | C12Q 1/6874 |

OTHER PUBLICATIONS

Potapov et al., Examining Sources of Error in PCR by Single-Molecule Sequencing. PLOS ONE, DOI:10.1371/journal.pone. 0169774, published on Jan. 6, 2017.*

Pezza et al., Polymerase Fidelity: What is it, and what does it mean for your PCR? New England Biolabs GmbH, neb-oline.de, pp. 1-3, 2014.*

Liu et al., Highly efficient one-step PCR-based mutagenesis technique for large plasmids using high-fidelity DNA polymerase. Genetics and Molecular Research, 14, 3466-3473, 2015.*

Beckman Coulter, Inc., "SPRIselect User Guide," PN B24965AA, Oct. 2012, 30 pages.

GenScript, "Gene Synthesis Handbook", Third Edition, Sep. 2016, 20 pages.

Guatelli et al., "Isothermal, in vitro amplification of nucleic acids by a multienzyme reaction modeled after retroviral replication," PNAS USA, Mar. 1990, 87(5):1874-1878.

Guatelli et al., "Isothermal, in vitro amplification of nucleic acids by a multienzyme reaction modeled after retroviral replication," PNAS USA, Oct. 1990, 87(19):7797.

Kwoh et al., "Transcription-based amplification system and detection of amplified human immunodeficiency virus type 1 with a bead-based sandwich hybridization format," PNAS USA, Feb. 1989, 86(4):1173-1177.

Kwon et al., "Emergence of synthetic mRNA: In vitro synthesis of mRNA and its applications in regenerative medicine," Biomaterials, 2018, vol. 156, pp. 172-193.

Li et al., "BEAMing up for detection and quantification of rare sequence variants," Nature Methods, Feb. 2006, vol. 3, No. 2, pp. 95-97.

Li et al., "Replacing PCR with COLD-PCR enriches variant DNA sequences and redefines the sensitivity of genetic testing," Nature Medicine, May 2008, vol. 14, No. 5, pp. 579-584.

Miele et al., "Autocatalytic Replication of a Recombinant RNA," J. Mol. Biol., 1983, 171, 281-295.

Tian et al., "Advancing high-throughput gene synthesis technology," Mol. BioSyst., (2009) 5, 714-722.

Young et al., "Two-step total gene synthesis method," Nucleic Acids Research, 2004, vol. 32, No. 7, e59, 6 pages.

Stemcell Technologies Inc., "ArciTect™ T7 Endonuclease I Kit," Stemcell Technologies, 2019, Document #DX21663, Version 1_4_0, 4 pages.

* cited by examiner

Method for synthesis of dsDNA fragments from oligos

Method for reducing error-rate in assembled dsDNA fragments

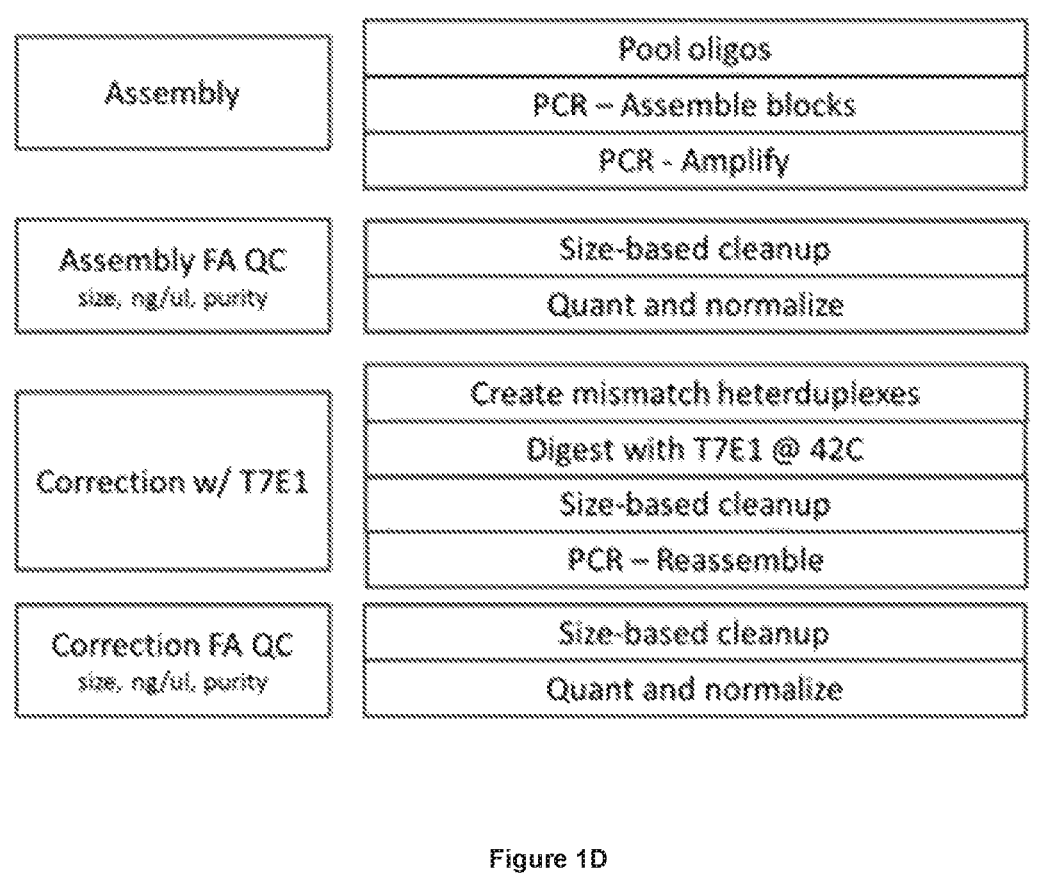

| Assembly | Pool oligos |
| | PCR – Assemble blocks |
| | PCR – Amplify |

| Assembly FA QC size, ng/uL, purity | Size-based cleanup |
| | Quant and normalize |

| Correction w/ T7E1 | Create mismatch heterduplexes |
| | Digest with T7E1 @ 42C |
| | Size-based cleanup |
| | PCR – Reassemble |

| Correction FA QC size, ng/uL, purity | Size-based cleanup |
| | Quant and normalize |

Figure 1D

Small – 40-60 bp

Medium – 60-100 bp

Large – 100-200 bp

Ultrapure – 60-100 bp

Raw
Assembly   Purified

Size selective purification impacts error reduction

□ uncorrected
▨ single round with gel purification post assembly
▩ single round with column purification post assembly
■ two rounds with column purification post assembly Error rates following endonuclease-mediated error correction in 24 gene fragments

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: PCR primer sequence

<400> SEQUENCE: 1
tcaagctttt ggaccctcgt acag                                    24

<210> SEQ ID NO 2
<211> LENGTH: 28
<212> TYPE: DNA
<213> ORGANISM: Artificial Sequence
```

-continued

```
<220> FEATURE:
<223> OTHER INFORMATION: PCR primer sequence

<400> SEQUENCE: 2
tcttccatgg tggctcttat atttcttc                                        28

<210> SEQ ID NO 3
<211> LENGTH: 26
<212> TYPE: DNA
<213> ORGANISM: Artificial Sequence
<220> FEATURE:
<223> OTHER INFORMATION: PCR primer sequence

<400> SEQUENCE: 3
gtgctacccg aggaattcat aatcag                                          26
```

ASSEMBLY AND ERROR REDUCTION OF SYNTHETIC GENES FROM OLIGONUCLEOTIDES

CROSS REFERENCE TO RELATED APPLICATIONS

This application is a U.S. National Phase application, filed under U.S.C. § 371, of International Application No. PCT/US2019/022918, filed Mar. 19, 2019, which claims priority to, and the benefit of, U.S. Provisional Application No. 62/644,919, filed on Mar. 19, 2018, the contents of each of which are incorporated herein by reference in their entireties.

INCORPORATION BY REFERENCE OF SEQUENCE LISTING

The contents of the text file named "MRNA-052-N01US_SeqList", which was created on Sep. 17, 2020 and is 945 bytes in size, are hereby incorporated by reference in their entireties.

BACKGROUND OF THE INVENTION

As gene therapy and molecular tools have evolved, the use of synthetic genes has become more important. While early applications used sequences that could be amplified from natural sources, the importance of sequence context has required genes to be recoded for maximized performance. These novel sequences must be synthesized from scratch. Modern methods of gene synthesis generally follow the same steps: chemical synthesis of oligonucleotides, enzymatic assembly and amplification of full length product, and enzymatic reduction of errors. Key to this process is the error reduction, as the chemical synthesis of oligonucleotides has a relatively high error rate, which limits the size of genes that can be reliably synthesized. Commercial suppliers of synthetic genes employ proprietary methods to synthesize genes, however these methods produce genes that have an error rate not compatible with assembling larger genes in an efficient manner.

Hence, there exist a need for a high-fidelity process for the chemical synthesis of a gene of interest with minimal sequence errors introduced by the synthesis process. The present invention addresses this need by providing such a process, leading up to an error rate reduction from an average of one error per 961 bp in assembled products that does not undergo error reduction to one per 4198 bp for those that are subjected to the complete process.

SUMMARY OF THE INVENTION

In one aspect, the present invention relates to a process for synthesizing a gene of interest, the process comprising the steps of:
    a. performing at least one segmenting/factoring step on at least one nucleotide sequence comprising an open reading frame (ORF) encoding a gene of interest to obtain a first pool of oligonucleotides;
    b. assembling and amplifying gene segments from said first pool of oligonucleotides.
    c. purifying the assembled and amplified gene segments;
    d. denaturing the purified gene segments into single stranded nucleic acid sequences and allowing random pairing of complementary strands, wherein paired complementary strands or gene segments comprise mismatched base pairs;
      i. Mismatch digesting the gene segments comprising mismatched base pairs to obtain digest fragments;
      ii. Purifying the digest fragments to obtain error-free gene segments; and,
    e. amplifying and assembling the error-free gene segments into a gene of interest, thereby synthesizing the gene of interest.

In one related aspect, the present invention relates to a process for reducing base pair error rate in the synthesis of a gene of interest, the process comprising the steps of:
    a. obtaining a pool of assembled gene segments confirmed to contain mismatch errors;
    b. denaturing the purified gene segments into single stranded nucleic acid sequences and allowing random pairing of complementary strands, wherein the paired complementary strands or gene segments comprise mismatched base pairs;
      i. mismatch digesting the gene segments comprising mismatched base pairs to obtain digest fragments;
      ii. purifying the digest fragments according to size to obtain error-free gene segments; and,
    c. amplifying the error-free gene segments;
      iii. purifying the error-free gene segments of interest, thereby reducing base pair error rate in the chemical synthesis of a gene of interest.

In another related aspect, the present invention relates to a process for synthesizing a gene of interest, the process comprising the steps of:
    a. segmenting at least one nucleotide sequence comprising an open reading frame (ORF) encoding a gene of interest;
    b. factoring the segments from the at least one nucleotide sequence to obtain a first pool of oligonucleotides;
    c. assembling the first pool of oligonucleotides into gene segments;
      i. providing a second pool of oligonucleotides for assembling and amplifying the gene segments;
    d. purifying the assembled and amplified gene segments;
    e. heteroduplexing the purified gene segments in step d. to form mismatched base pairs;
      i. mismatch digesting the gene segments comprising mismatched base pairs to obtain digest fragments;
      ii. purifying the digest fragments to obtain error-free gene segments;
    d. amplifying the error-free gene segments;
      i. Purifying the error-free gene segments of interest; and,
    f. assembling the gene segments of interest into a gene of interest, thereby synthesizing the gene of interest.

In another related aspect, the present invention relates to a process for reducing base pair error rate in the synthesis of a gene of interest, the process comprising the steps of:
    a. obtaining a pool of assembled gene segments confirmed to contain mismatch errors;
    b. heteroduplexing the gene segments to form mismatched base pairs;
      i. mismatch digesting the gene segments comprising mismatched base pairs to obtain digest fragments;
      ii. purifying the digest fragments to obtain error-free gene segments;
    c. amplifying the error-free gene segments; and,
      i. purifying the error-free gene segments of interest, thereby reducing base pair error rates in the chemical synthesis of a gene of interest.

In one embodiment, the synthesis of the gene of interest comprises a chemical synthesis of the gene of interest.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

Any of the above aspects and embodiments can be combined with any other aspect or embodiment.

Unless otherwise defined, all technical and scientific terms used herein have the same meaning as commonly understood by one of ordinary skill in the art to which this invention belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the invention will be apparent from the following detailed description and claim.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawing wherein:

FIG. 1A-D illustrates a Gene synthesis process summary. FIG. 1A. Desired genes are factored into segments, and segments into oligos. Oligos are synthesized and assembled into the full length segment via polymerase chain assembly and polymerase chain reaction (PCR). Segments can then be assembled into plasmids as full length genes via downstream processes. FIG. 1B. As synthesized oligos have inherent errors, which propagate in the assembled segments, the errors must be reduced to enable efficient cloning of error free genes. Gene segments are heteroduplexed to form mismatches, and enzymes that detect and digest the segments at the mismatches are used to reduce the errors. Digested fragments are then reassembled into the desired segment via PCR. FIG. 1C. Demonstration of 10 gene segments synthesized by the current process. Error rates were reduced from an average of one error per 961 bp in assembled products that did not undergo error reduction to one per 4198 bp for those that were subjected to the complete process. FIG. 1D. A flow chart illustrating one embodiment of the processes of the disclosure.

FIG. 3A shows three polymerases that were used to assemble and amplify oligos for six different gene segments in triplicate. FIG. 3B shows six gene segments that were assembled from oligos and amplified by Q5 polymerase, with annealing temperatures ranging from 45° C. to 65° C.

FIG. 4A. Low molecular weight contaminants are removed from the amplified assembly product via SPRI purification. FIG. 4B. Oligo pools for 6 genes were assembled, purified, and corrected as indicated. Two rounds of error reduction with non-size selective column purification were necessary to produce similar results as a single round with gel purification of the target band.

FIG. 5A: multiple enzymes were compared for removing errors in two genes. While all 3 performed similarly at their recommended incubation temperature, combining two enzymes at an alternate temperature unexpectedly improved error reduction. FIG. 5B: T7E1 was used to reduce the errors in two genes. While the recommended temperature is 37° C., superior results were unexpectedly achieved at elevated temperatures.

FIG. 8A shows the impact of DNA length on percent recovery of DNA using SPRI beads. PCR products of 100 bp and 700 bp in length were generated, column purified and eluted in water. Various ratios of 100 bp:700 bp product (by mass) were prepared in a total volume of 50 µL and purified using SPRI, eluted in water, and run on a fragment analyzer to quantify % of total purified DNA that was 700 bp in length. SPRI was performed using Sera-mag beads (20 µL of bead solution per ml SPRI buffer) that were washed once in water and re-suspended in buffer D (20%

PEG8000, 2 M salt, 10 mM Tris pH 8, 1 mM EDTA). FIG. 8B shows EPO, CA1, CA2 and CA3 gene fragments that were generated from oligos by assembly and amplification PCR, followed by T7E1 error correction. Samples of each fragment (before and after SPRI purification) were run on 1% agarose gels to visualize the presence and/or absences of smaller fragments (oligos, primers, short byproducts). FIG. 8C shows the CA1 DNA fragment was generated from oligos by assembly and amplification PCR followed by error correction. Samples of each fragment (before and after SPRI purification) were run on 1% agarose gels to visualize presence and/or absences of smaller fragments (oligos, primers, short byproducts).

FIG. 10A shows a diagram of oligo coverage of a 550 base pair gene fragment. Three variable regions targeted for mutagenesis are indicated with asterisks. FIG. 10B is a gel showing the successful synthesis of 84 mutants using the methods of the disclosure.

DETAILED DESCRIPTION

Figure 1A:
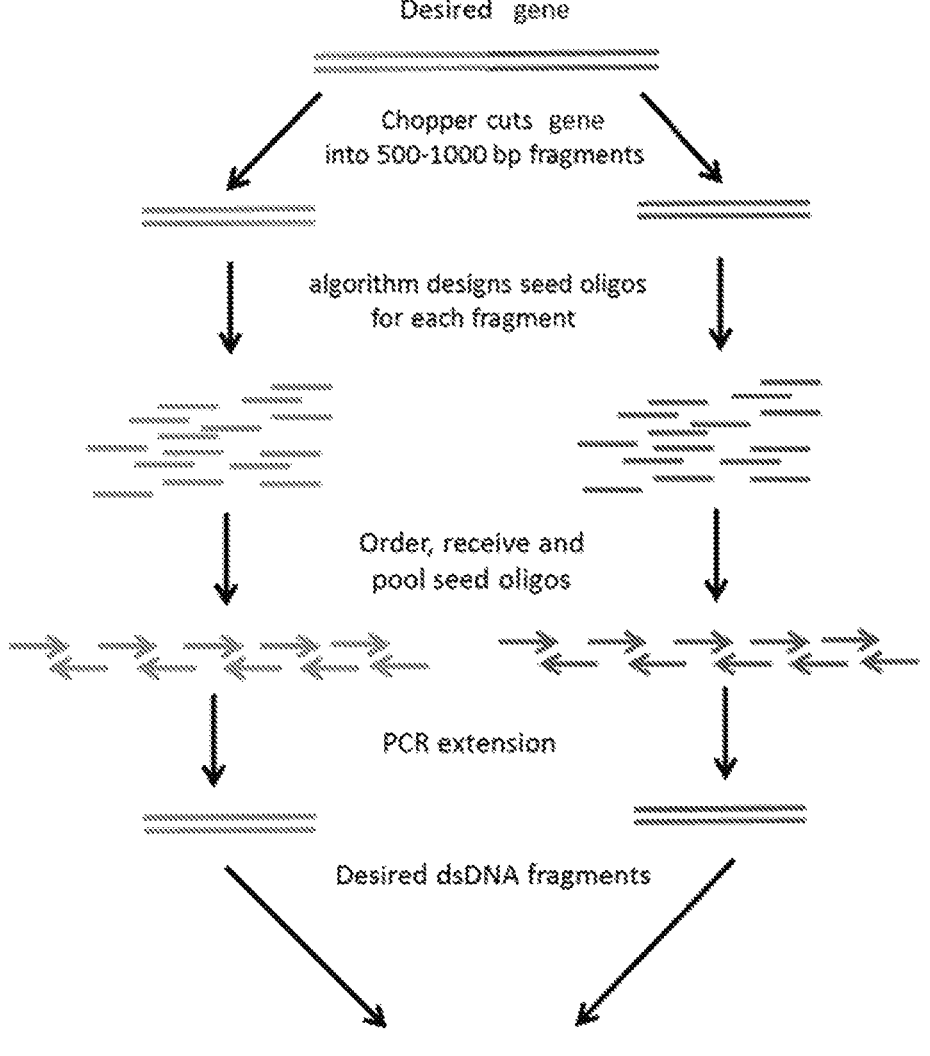
Figure 1B:
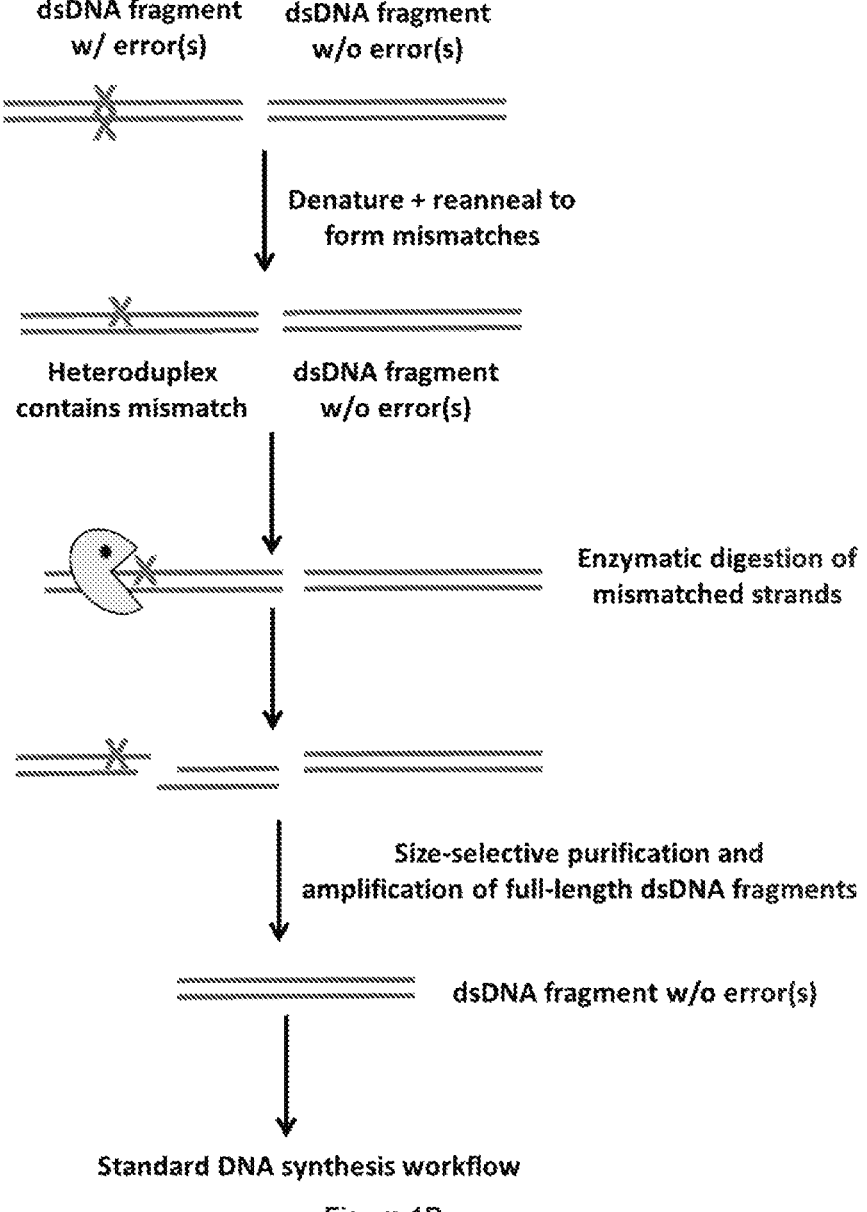
Figure 1C:
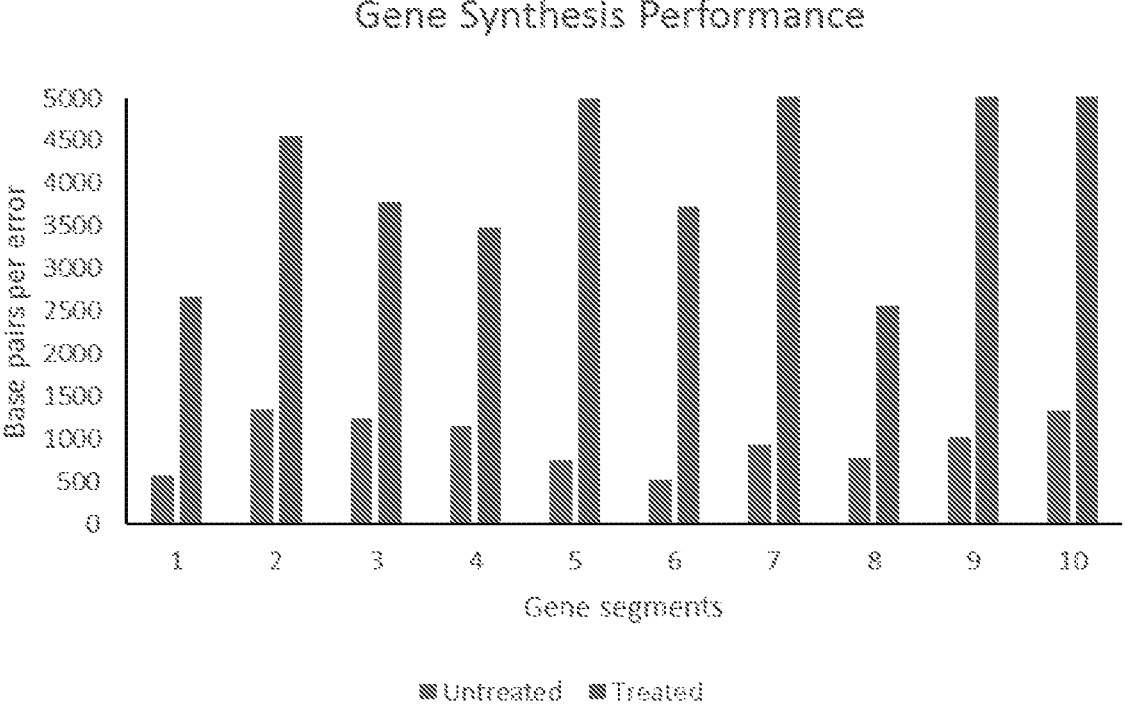

The present disclosure provides rapid, high-fidelity processes or methods to support synthesis of genes for a variety of applications, including, but not limited to, in vitro transcription of modified messenger RNA, mutagenesis experiments and generation of synthetic gene constructs.

Synthesis of gene fragments from oligos, without some form of error correction, frequently leads to the introduction of errors in the final product. These errors can be, for example, insertions, deletions or base pair substitutions. Depending on the vendor and purity, commercially synthesized oligos have an error rate of about 1 error per every 400 to 900 base pairs synthesized. Polymerases, which are used to assemble and amplify gene fragments during synthesis, are also sources of errors. Even high fidelity polymerases with proofreading activity can introduce errors at a rate of about 1 error per 3,500 base pairs to about $1 \times 10^6$ base pairs synthesized. Depending on the size of the gene fragment being synthesized, this can make it extremely difficult and time consuming to synthesis and isolate gene fragments that are error-free. There thus exists a need in the art for improved methods of gene synthesis that reduce or eliminate errors during gene fragment synthesis. The methods of the disclosure address this need.

In some embodiments of the methods of the disclosure, the methods lead to an error rate during gene fragment synthesis that is less than about 1 error per 1,500 base pairs synthesized, less than about 1 error per 2,000 base pairs synthesized, less than about 1 per 2,500 base pairs synthesized, less than 1 error per 3,000 base pairs synthesized, less than about 1 error per 3,500 base pairs synthesized, less than about 1 error per 4,000 base pairs synthesized, less than about 1 error per 4,500 base pairs synthesized, less than about 1 error per 5,000 base pairs synthesized, less than about 1 error per 5,500 base pairs synthesized, less than about 1 error per 6,000 base pairs synthesized, less than about 1 error per 6,500 base pairs synthesized, less than about 1 error per 7,000 base pairs synthesized, less than about 1 error per 7,500 base pairs synthesized, less than about 1 error per 8,000 base pairs synthesized, less than about 1 error per 8,500 base pairs synthesized, less than about 1 error per 9,000 base pairs synthesized, less than about 1 error per 9,500 base pairs synthesized, less than about 1 error per 10,000 base pairs synthesized, less than about 1 error per 11,000 base pairs synthesized, less than about 1 error per 12,000 base pairs synthesized, less than about 1 error per 13,000 base pairs synthesized, less than about 1 error per 15,000 base pairs synthesized or less than about 1 error per 20,000 base pairs synthesized.

In some embodiments of the methods of the disclosure, the methods lead to an error rate during gene fragment synthesis that is less than about 1 error per 5,000 base pairs synthesized.

In some embodiments of the methods of the disclosure, the methods lead to an error rate during gene fragment synthesis that is less than about 1 error per 7,000 base pairs synthesized.

In some embodiments of the methods of the disclosure, the methods lead to an error rate during gene fragment synthesis that is less than about 1 error per 8,000 base pairs synthesized.

In some embodiments of the methods of the disclosure, the methods lead to an error rate during gene fragment synthesis that is less than about 1 error per 10,000 base pairs synthesized.

Depending on the size of the gene fragment being synthesized, the reduced error rates of the methods of the disclosure can reduce synthesis time and expense. Furthermore, the reduced error rates of the disclosure allow for the synthesis of longer gene fragments. For example, when synthesizing a 3,000 gene fragment using the methods of the disclosure with an error rate of less than about 1 error per 5,000 base pairs synthesized, the person of ordinary skill in the art would expect to screen only a small number of individual DNA molecules to arrive at one that was without errors. As screening of synthesized gene fragments can involve PCR amplification, cloning into a plasmid, bacterial transformation, culturing bacterial clones, prepping DNA and sequencing, this represents a substantial reduction in work and increase in time saved. For larger gene fragments, the number of individual DNA molecules that would have to be cloned and sequenced to arrive at an error free synthesized fragment can be prohibitively large without error correction, such as that provided by the methods of the instant disclosure.

As demonstrated by the working examples disclosed herein, use of these methods leads to error rates that were surprisingly reduced from an average of one error per 961 bp in assembled products that did not undergo error reduction to one per 4198 bp for those that were subjected to the complete process of the invention. In some of the working examples disclosed herein, error rates were reduced to less than 1 in about 5,000 base pairs. In some of the working examples disclosed herein, error rates were reduced to less than 1 in about 7,000 base pairs. n some of the working examples disclosed herein, error rates were reduced so low as to be undetectable.

Definitions

The term "process" and "method" or grammatical equivalents thereof when used with respect to the disclosed process or method of synthesizing a gene of interest, are synonymously utilized in the present invention disclosed herein.

An "open reading frame" is a continuous stretch of DNA beginning with a start codon (e.g., methionine (ATG)), and ending with a stop codon (e.g., TAA, TAG or TGA) and encodes a protein or peptide. In some embodiments, a gene of interest assembled by the process of the invention comprises DNA.

A "nucleic acid insert" herein refers to a nucleic acid comprising (or consisting essentially of) the following contiguous genetic elements, arranged in the 5' to 3' direction: a 5' untranslated region, an open reading frame and a 3' untranslated region. In some embodiments, an insert further comprises (or consists essentially of) a 3' polyA sequence (e.g., a sequence consisting of ten or more consecutive adenosine monophosphates).

A "nucleic acid" is at least two nucleotides covalently linked together, and in some instances, may contain phosphodiester bonds (e.g., a phosphodiester "backbone"). The term encompasses deoxyribonucleic acid (DNA) and ribonucleic acid (RNA). An "engineered nucleic acid" is a nucleic acid that does not occur in nature. It should be understood, however, that while an engineered nucleic acid as a whole is not naturally occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell.

For the purposes of this invention, the terms "oligos", "oligonucleotide", "polynucleotide" and "nucleic acid" are used interchangeably, unless otherwise noted and refer to at least two nucleotides, ribonucleotides and/or deoxyribonucleotides or a modified form of either type of nucleotides, covalently linked together. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. A "nucleotide" refers to a sub-unit of a nucleic acid and has a phosphate group, a carbon sugar and a nitrogen containing base, as well as functional analogs (whether synthetic or naturally occurring) of such sub-units which in the polymer form (as a polynucleotide) can hybridize with naturally or non-naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides. The term "nucleotide" refers to a nucleoside having a phosphate group on its 3' or 5' sugar hydroxyl group. These nucleotide units may be nucleic acid bases such as guanine, adenine, cytosine, thymine or uracil. The sugar group can be a deoxyribose or ribose. Nucleic acids refer to both naturally occurring and synthetic species formed from naturally occurring subunits. Nucleotides useful in the invention include, for example, naturally-occurring nucleotides (for example, ribonucleotides or deoxyribonucleotides), or natural or synthetic modifications of nucleotides, or artificial bases. An oligonucleotide synthesized according to the invention, generally contains plosophodiester bonds, although it may contain alternate backbones comprising for example, phosphoramide, phosphorothioate, phosphorodithioate, O-methylphosphoroamidite linkages, non-ionic backbones, non-ribose backbones, peptide nucleic acid backbones and linkages. Nucleic acids include peptide nucleic acids and locked nucleic acids.

A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing. Non-limiting examples of a synthetic nucleic acid include a gene segments or genes of interest disclosed herein that are chemically engineered. The process of the invention may include engineering nucleic acids using standard molecular biology methods (see, e.g., Green and Sambrook, Molecular Cloning, A Laboratory Manual, 2012, Cold Spring Harbor Press). Other non-limiting examples of synthetic nucleic acids include oligonucleotides or primers, such as those of the invention which are designed to consider the uniqueness of the chosen overlap sequence within the sequence as a whole.

A "vector" is a nucleic acid (e.g., DNA) used as a vehicle to artificially carry genetic material (e.g., a nucleic acid insert). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which typically includes nucleotide overhangs for insertion of a nucleic acid insert, and multiple endonuclease recognition sites to either side of the insert. In one embodiment, the gene segments produced by the process of the invention can be assembled into one or more plasmids using DNA synthesis methods readily available in the art.

The term "polymerase cycling assembly" refers to such a method that involves stepwise extending oligonucleotide fragments hybridized by overlapping at both ends through heat cycle reaction by directly using thermophilic DNA polymerase, and finally synthesizing the full length gene.

The term "mismatch-specific endonuclease" refers to an enzyme that can cleave all types of DNA double-strand mismatches caused by base mutation, insertion or deletion.

The term "segmenting" or grammatical equivalents thereof refers to a nucleic acid sequence of interest or gene that can be parsed into smaller length segments of sequences that together comprise the nucleic acid sequence of interest. For example, in a first step, sequence information can be obtained. The sequence information may be the sequence of a nucleic acid of interest that is to be assembled. As a non-limiting example, a nucleic acid of the invention is sectioned into segments of up to about 1000 based pairs (bp) with about 30 bp overlaps between segments.

The term "factoring" or grammatical equivalents thereof refers to a segment of nucleic acid sequence or segment of a gene that can be parsed into a set of smaller lengths of oligonucleotides that together comprise the segment of the nucleic acid sequence or gene. As a non-limiting example, a nucleic acid sequence or gene segment of the invention is factored into oligonucleotides with lengths of 60 to 90 bases, with overlaps of about 20 bases and a GC content of about 48-52%.

In some embodiments the terms "factoring" and "segmenting" overlap in meaning with the term "fragmenting" or its grammatical equivalents, which refers to reducing a nucleic acid disclosed herein to a smaller sized or smaller length (in terms of base pairs, for e.g.) portion.

The term "gene of interest" refers to a polynucleotide which encodes a polypeptide or protein of interest. Depending on the context, the gene of interest refers to a deoxyribonucleic acid, e.g., a gene of interest in a DNA template which can be transcribed to an RNA transcript, or a ribonucleic acid, e.g., a gene of interest in an RNA transcript which can be translated to produce the encoded polypeptide of interest in vitro, in vivo, in situ or ex vivo. A polypeptide of interest includes but is not limited to, biologies, antibodies, vaccines, therapeutic proteins or peptides, etc.

The term "digest" means to break apart into smaller pieces or components. When referring to polypeptides or proteins, digestion results in the production of peptides. When referring to DNA or mRNA, digestion results in the production of oligonucleotide fragments.

As used herein, embodiments of the invention are "engineered" when they are designed to have a feature or property, whether structural or chemical, that varies from a starting point, wild type or native molecule.

The term "expression" of a nucleic acid sequence refers to one or more of the following events: (1) production of an RNA template from a DNA sequence {e.g., by transcription); (2) processing of an RNA transcript {e.g., by splicing, editing, 5' cap formation, and/or 3' end processing); (3) translation of an RNA into a polypeptide or protein; and (4) post-translational modification of a polypeptide or protein.

The term "modified" refers to a changed state or structure of a molecule of the invention. Molecules can be modified in many ways including chemically, structurally, and functionally. In one embodiment, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides. Modifications according to the present invention can be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

The term "open reading frame" or "ORF" refers to a sequence which does not contain a stop codon in a given reading frame.

The phrase "operably linked" refers to a functional connection between two or more molecules, constructs, transcripts, entities, moieties or the like. For example, a gene of interest operably linked to an RNA polymerase promoter allows transcription of the gene of interest.

The term "purify," "purified," "purification" means to make substantially pure or clear from unwanted components, material defilement, admixture or imperfection.

The term "RNA transcript" refers to a ribonucleic acid produced by an in vitro transcription reaction using a DNA template and an RNA polymerase. As described in more detail below, an RNA transcript typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, mRNA "mmRNA" or modified mRNA, and primary construct.

The term "synthetic" means produced, prepared, and/or manufactured by the hand of man. Synthesis of polynucleotides or polypeptides or other molecules of the present invention can be chemical or enzymatic.

The term "unmodified" refers to any substance, compound or molecule prior to being changed in any way. Unmodified can, but does not always, refer to the wild type or native form of a biomolecule. Molecules can undergo a series of modifications whereby each modified molecule can serve as the "unmodified" starting molecule for a subsequent modification.

Synthesis of Gene of Interest

To design a nucleotide sequence for optimal assembly, a nucleic acid sequence encoding a gene of interest may be broken down into a defined number of smaller fragments with optimal hybridization properties by means of an algorithm taking into account parameters such as melting temperature, overlap regions, self-hybridization, absence or presence of cloning sites and the like. In some embodiments, the algorithm factors the sequence into <1 kb blocks with overlaps that are optimized for isothermal assembly, and each block is factored into oligos with overlaps that are optimized for PCR assembly.

In certain aspects of the invention, at least part of the desired nucleic acid sequence may encode a polypeptide or protein. In such cases, it may be desirable to optimize the open reading frame for improved performance in a given homologous or heterologous host, such as expression yield or solubility. An increase in gene expression may be achieved, for example, by replacing non-preferred or less preferred codons by preferred codons or by increasing the number of CpG dinucleotides in the open reading frame as described, for example, in U.S. Pat. Nos. 5,786,464 and 6,114,148 and U.S. Patent Publication No. 2009/0324546 AA, the disclosures of which are incorporated herein by reference. In certain aspects of the invention, at least part of the desired nucleic acid sequence may encode a non-coding RNA. In certain aspects of the invention, at least part of the desired nucleic acid sequence may encode a chimeric, synthetic or mutant protein or non-coding RNA. The synthesis methods of the disclosure provide superior flexibility in the design and execution of gene fragments or constructs.

Once the chemical synthesis phase of the invention has been completed, the resulting nucleic acid molecules may be assembled, if desired, into larger nucleic acid molecules. Depending on the end purpose for which the final nucleic acid molecules are to be used, the "quality" (e.g., from a sequence fidelity perspective) of the chemically synthesized nucleic acid molecules may be too low for the intended application. As an example, if the chemically synthesized nucleic acid molecules are to be used as long probes, then they may be of sufficient quality for that purpose without further processing. However, consider the situation where one hundred nucleic acid segments are to be assembled, each nucleic acid segment is one hundred base pairs in length and there is one error per fifty base pairs. The net result is that there will be, on average, 200 sequence errors in each 10,000 base pair assembled nucleic acid molecule. If one intends, for example, to express one or more proteins from the assembled nucleic acid molecule, then the number of sequence errors would likely be considered to be too high. Also, while sequencing of individual nucleic acid molecules may be performed, this is time consuming and involves additional cost. Thus, in many instances, an error removal step may be performed. Typically, this will be performed after a first round of assembly and in such cases, the process of reducing errors of the invention may be employed. Thus, in one embodiment, methods of the invention involve the following (in this order or different orders):

1. Fragment Amplification and Assembly (e.g., in vitro assembly/PCR).
2. Error Correction.
3. Final Assembly (e.g., in vivo assembly).

In one particular embodiment, provided is a process for synthesizing a gene of interest, the process comprising the steps of:

a. performing at least one segmenting/factoring step on at least one nucleotide sequence comprising an open reading frame (ORF) encoding a gene of interest to obtain a first pool of oligonucleotides;

b. assembling and amplifying gene segments from said first pool of oligonucleotides.

c. purifying the assembled and amplified gene segments;

d. denaturing the purified gene segments into single stranded nucleic acid sequences and allowing random pairing of complementary strands, wherein paired complementary strands or gene segments comprise mismatched base pairs;

i. mismatch digesting the gene segments comprising mismatched base pairs to obtain digest fragments;

ii. purifying the digest fragments to obtain error-free gene segments; and, e. amplifying and assembling the error-free gene segments into a gene of interest, thereby synthesizing the gene of interest.

In one embodiment, the invention requires the use of at least one purification step in order to confirm that the purified gene segments are assembled into a segment of correct size and concentration at various steps of the gene synthesis process. In another embodiment, the amplified error-free gene segments of the invention are purified to confirm that they are of the correct size and concentration. A purification step of the invention can be carried out using conventional means readily available in the art to the skilled artisan, which include but are not limited to, solid phase reversible immobilization (SPRI), size-selective purifications, such as gel excision and size selective SPRI. In one particular embodiment, purifications using gel excision and size selective SPRI were shown to be superior in minimizing errors propagating to the final product (see Examples herein).

In some embodiments, the invention requires the use of at least one size-based purification step in order to separate completely assembled and amplified gene fragments from non-assembled oligos or smaller partially assembled byproducts of the reaction. Size-based purification can be carried out by any methods known in the art, including, but not limited to, excising and extracting nucleic acids from bands in a gel, and solid phase reversible immobilization (SPRI) beads. In some embodiments, the SPRI separation can separate longer assembled gene fragments from shorter oligos in the reaction. In some embodiments, the assembled gene fragments are at least 400 bp, at least 500 bp, at least 600 bp, at least 700 bp or at least 800 bp in length and the shorter oligos are less than 200 bp or less than 100 bp in length. In some embodiments, SPRI was performed using Sera-mag beads (20 μL of bead solution per ml SPRI buffer) that were washed once in water and re-suspended in a buffer. In some embodiments the buffer comprised or consisted of 20% PEG8000, 2 M salt, 10 mM Tris pH 8 and 1 mM EDTA (buffer D). In some embodiments, assembled gene fragments were bound to the SPRI beads in buffer D by adding 50 μL of SPRI+Buffer to 50 μL of DNA. In some embodiments, the assembled and amplified gene fragments are SPRI purified prior to heteroduplexing and error correction. In some embodiments, the assembled and amplified gene fragments are SPRI purified after heteroduplexing and error correction. In some embodiments, the assembled and amplified gene fragments are SPRI purified both before and after heteroduplexing and error correction. SPRI purification is significantly faster than gel-excision based purification methods. SPRI purification has the further advantage of being compatible with a variety of automated (i.e., high throughput) platforms, allowing for the purification of gene fragments in 96 well plate format, e.g.

In some embodiments, the process for synthesizing the gene of interest further comprises repeating the sequential steps of denaturing, amplifying and assembling the gene of interest (steps d.-e.) to achieve optimum fidelity in reducing mismatch errors in the gene segments.

In one embodiment, the nucleotide sequences are sectioned into segments of up to 2000 base pairs comprising about 15-50 base pair overlaps between segments.

The target nucleic acid can be obtained from any sample or source of nucleic acid, e.g., any cell, tissue, or organism, in vitro, chemical synthesizer, and so forth. The target nucleic acid can be obtained by any art-recognized method. In embodiments, the nucleic acid is obtained from a blood sample of a clinical subject. The nucleic acid can be extracted, isolated, or purified from the source or samples using methods and kits well known in the art.

A nucleic acid molecule comprising the target nucleic acid may be fragmented by any means known in the art. Preferably, the fragmenting is performed by an enzymatic or a mechanical means. The mechanical means may be sonication or physical shearing. The enzymatic means may be performed by digestion with nucleases (e.g., Deoxyribonuclease I (DNase I)) or one or more restriction endonucleases.

The target nucleic acid encoding a gene segment of interest or gene of interest can include natural or non-natural nucleotides, comprising modified nucleotides, as well-known in the art.

In some embodiment, at least one oligonucleotide of the methods provided herein comprises about 40 to 250 bases in length. In other embodiments, at least one oligonucleotide comprises about 50-240, 60-230, 70-220, 80-210, 90-200, 100-200, 110-190 bases in length. In other embodiments, at least one oligonucleotide comprises about 30-260, 20-270 or 20-300 or 20-400 or 20-500 bases in length. In a particular embodiment, at least one oligonucleotide comprises about 60-90 bases in length. In a particular embodiment, at least one oligonucleotide comprises about 60-100 bases in length.

In some embodiments, at least one oligonucleotide of the methods provided herein comprises an overlap region of about 20-50 base pairs. In other embodiments, at least one oligonucleotide comprises an overlap region of about 25-45, 30-40, or 35-45 base pairs. In other embodiments, at least one oligonucleotide comprises an overlap region of 15-25 base pairs. In other embodiments, at least one oligonucleotide comprises an overlap region of 20 base pairs.

In some embodiments, the overlap region comprises a GC content of about 40-60%. In other embodiments, the overlap region comprises a GC content of about 35-65%. In other embodiments, the overlap region comprises a GC content of about 45-55%, 46-54%, 47-53%, 48-52%, or 49-51%.

In one embodiment, an algorithm provided herein (see working examples) is used to design the overlaps between sections as well as between oligonucleotides to consider the uniqueness of the chosen overlap sequence within the sequence as a whole. In some embodiment, the invention employs the use of an algorithm to design oligonucleotides for the high fidelity polynucleotide assembly. Embodiments of the invention may be useful to increase the throughput rate of a nucleic acid assembly procedure and/or reduce the number of steps or amounts of reagent used to generate a correctly assembled nucleic acid sequence having a pre-defined sequence. Embodiments of the invention may be useful in the context of automated nucleic acid assembly to reduce the time, number of steps, amount of reagents, and other factors required for the assembly of each correct nucleic acid sequence. Accordingly, these and other embodiments of the invention may be useful to reduce the cost and time of one or more nucleic acid assembly procedures.

The oligonucleotides used in the methods of the invention can be synthesized using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

In one embodiment of the present invention, the oligonucleotides that are used for gene synthesis methods are high-fidelity oligonucleotides (average coupling efficiency is greater than 99.2%, or more preferably 99.5%). In one embodiment, the high-fidelity nucleotides are between 40-200 bases long. In a further embodiment the high-fidelity oligonucleotides are between 75-200 bases, and in a further embodiment 100-190 bases. In a further embodiment the high-fidelity oligonucleotides are between 60-100 bases. High-fidelity oligonucleotides are available commercially, even at greater lengths.

One skilled in the art would understand that to build an oligonucleotide of a particular length, a plurality of synthetic cycles is necessary. A synthetic cycle is repeated to add one monomer (e.g. nucleoside monomer unit) at a time to achieve the desired predefined sequence and length which define the oligonucleotide (e.g. oligonucleotide comprising X nucleotides).

In some embodiments, libraries of oligonucleotides are synthesized. In some embodiments, at least 100, at least 1000, at least 10,000, at least 100,000, at least $10^6$ or more oligonucleotides can be synthesized on a single array.

Spurious chemical reactions cause random base errors in oligonucleotides. A sequence error may include one or more nucleotide deletions, additions, substitutions (e.g., transversion or transition), inversions, duplications, or any combination of two or more thereof. One of the critical limitations in chemical nucleic acid synthesis is the error-rate. The error rate of chemically-synthesized oligonucleotides (e.g. deletions at a rate of 1 in 100 bases and mismatches and insertions at about 1 in 400 bases) exceeds the error rate obtainable through enzymatic means of replicating an existing nucleic acid (e.g., PCR).

In some embodiments, the oligonucleotide sequences may be designed to include: amplification primer sequence(s), overlaps, recognition site for a restriction enzyme, such as an endonuclease, recognition site for a restriction enzyme (same or different restriction enzyme), and amplification primer sequence(s). The terms "amplification primer sequence", "primer binding site", "primer binding sequence" and "primer recognition site" are used interchangeably.

In some embodiments, the sequence information may first be analyzed to determine an assembly strategy.

In one embodiment, the first pool of oligonucleotides is assembled by using a second pool of oligonucleotides that are combined with the first pool of oligonucleotides in an equimolar ratio. In some embodiments, the at least one oligonucleotide from the second pool of oligonucleotides is at least partially complementary to at least one oligonucleotide from the first pool of oligonucleotides.

In one embodiment, the oligonucleotide assembling step (b.) in the process for synthesizing a gene of interest comprises using polymerase chain assembly (PCA) using the second pool of oligonucleotides to assemble the first pool of oligonucleotides into gene segments and polymerase chain reaction (PCR) to amplify the gene segments. In other embodiments, the assembled gene segments are amplified. In another embodiment, the assembling step (e.) comprises using PCR. In other embodiments the step of assembling gene segments of interest into a gene of interest comprises using PCR. In other embodiments, any step of amplifying disclosed herein comprises using PCR. In other embodiments, the step of assembling gene segments of interest into a gene of interest comprises using PCA.

In some embodiments, amplification primers (e.g., between 10 and 50 nucleotides long, between 15 and 45 nucleotides long, about 25 nucleotides long, etc.) corresponding to the flanking amplification sequences may be used to amplify the gene segments.

In one embodiment, the amplifying step e. comprises using PCR. In other embodiments, the assembling of step e. comprises using PCR. In other embodiments, the synthesized gene of interest comprises at least one exon sequence. In other embodiments, the synthesized gene of interest comprises at least one intron sequence. In other embodiments, the assembled gene segments comprise at least one exon sequence. In other embodiments, the assembled gene segments comprise at least one intron sequence. In some embodiments, amplification is performed with universal forward and reverse primers, and through multiple cycles of amplification a desired product (e.g., a gene segment disclosed herein) is formed. This product can then be diluted, and undergo further amplification that results in the desired gene.

In some embodiments of the methods of the disclosure, the assembly and amplification steps in the process for synthesizing a gene fragment of interest comprises using polymerase chain reaction (PCR). In some embodiments, the polymerase is Q5 polymerase. In some embodiments, the PCR comprises 60-100 bp oligos of greater than 90% purity with 20 base pair overlaps. In some embodiments, the PCR comprises 15 cycles for the assembly reaction. In some embodiments, the PCR comprises 25 cycles for the amplification reaction. In some embodiments, the combination of a 15 cycle assembly reaction and a 25 cycle amplification reaction produce yields of 15 ng/μL of DNA or greater. A PCR "cycle" will be readily apparent to a person of ordinary skill in the art.

Nucleic acid molecules assembled by methods of the invention may vary greatly and include molecules of at least 20 kilobases (e.g., between from about 0.5 kilobase and to about 10 megabases, between from about 0.5 kilobase and to about 5 megabases, between from about 0.5 kilobase and to about 1 megabase, between from about 0.5 kilobase and to about 500 kilobases, between from about 0.5 kilobase and to about 100 kilobases, between from about 0.5 kilobase and to about 10 megabases, between from about 0.5 kilobase and to about 1 kilobase, between from about 1 kilobase and to about 10 megabases, between from about 10 kilobases and to about 5 megabases, between from about 1 kilobase and to about 5 megabases, between from about 1 kilobase and to about 2 megabases, between from about 1 kilobase and to about 1 megabase, between from about 1 kilobase and to about 500 kilobases, between from about 10 kilobases and to about 1 megabases, between from about 10 kilobase and to about 500 kilobases, between from about 10 kilobase and to about 100 kilobases, etc.).

Nucleic acid molecules assembled by methods of the invention may be, for example, single stranded, partly single stranded or double stranded, closed, circular (e.g., a plasmid); nicked, circular; or linear (e.g., a plasmid, a chromosome, etc.). Further, methods of the invention may be performed such that two or more (e.g., two, three, four, five, six, ten, twenty, etc.) assembled nucleic acid molecules are simultaneously formed in the same reaction mixture.

The process of the invention may be applied for constructing gene segments up to 1000 base pairs in length. The process, however, can also be applied to other double stranded DNA templates such as PCR products or assembled plasmids. Also, while the process can be deployed in a single round, multiple rounds can be performed to remove more errors, which would be advantageous for synthesizing larger sequences, such as synthetic chromosomes. Furthermore, while temperature was used to improve the mismatch digestion properties of T7E1, chemical agents which decrease base pairing efficiency, such as di-methyl sulfoxide (DMSO) and Betaine, may be used to produce similar results at lower temperatures.

Figure 3A:
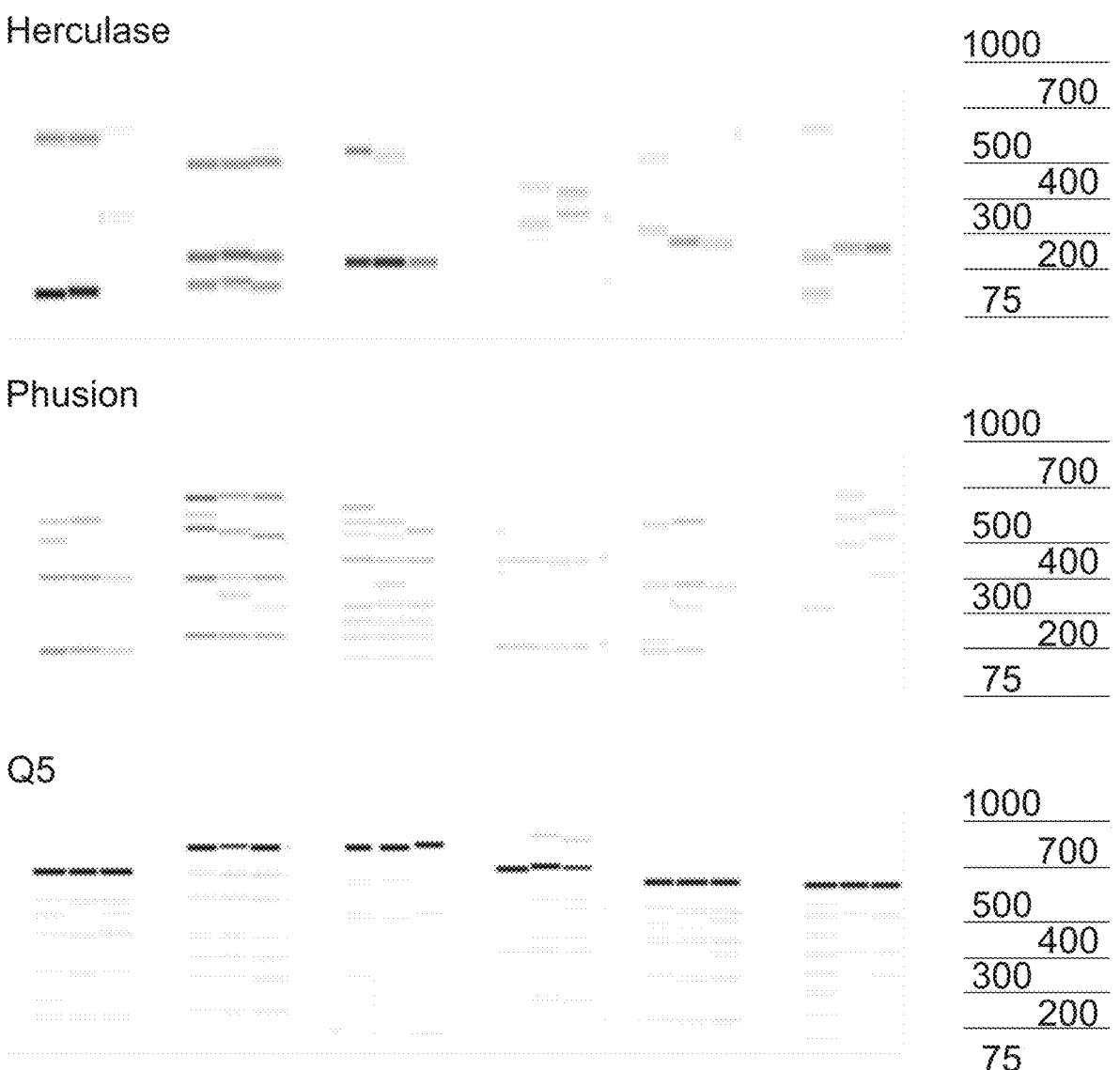
FIG. 3A-B illustrates oligo assembly and amplification.

In one embodiment, the methods of the invention further comprise the step of confirming that the purified gene segments in step e. are of correct size and concentration. In exemplary embodiments, a purification step of the invention comprises confirming that the gene segments generated by the process are of correct size and concentration and may be carried out using conventional means readily available to one of ordinary skill, including, but not limited to agarose gel electrophoresis, capillary electrophoresis, or other chromatographic methods. Likewise, concentration of the purified reassembly can be determined by multiple methods, including optical density (at appropriate wavelength), gel densitometry, or fluorescent intercalating dyes. In one embodiment, the present invention uses capillary electrophoresis to verify the size and purity of the segment (see FIG. 3A), and optical density at 260 nm to determine concentration.

As one skilled in the art would recognize, the amount of nucleic acid required to be produced will vary with, for examples, the application and the efficiency of assembly methods used. When a replicable molecule (e.g., via PCR, insertion into a cell, etc.) is generated, theoretically at least one assembled nucleic acid molecule is generated. Methods of the invention will typically be designed to generate from about 1 to about 500,000, from about 10 to about 500,000, from about 100 to about 500,000, from about 500 to about 500,000, from about 1 to about 1,000, from about 1 to about 500, from about 10 to about 1,000, from about 10 to about 500, from about 100 to about 1,000, from about 100 to about 500, from about 100 to about 5,000, from about 100 to about 50,000, from about 100 to about 250,000, from about 1,000 to about 50,000, etc. assembled nucleic acid molecules.

Methods of the invention may be used to generate from about 100 to about 20,000,000, from about 1,000 to about 20,000,000, from about 10,000 to about 20,000,000, from about 100 to about 5,000,000, from about 1,000 to about 5,000,000, from about 10,000 to about 5,000,000, from about 100 to about 1,000,000, from about 1,000 to about 1,000,000, from about 10,000 to about 10,000,000, from about 100 to about 500,000, from about 1,000 to about 500,000, from about 10,000 to about 500,000, etc. nucleic acid molecules designed to have the same nucleotide sequence.

It will be understood by the skilled artisan that the above methods can be re-ordered or altered, or further steps can be incorporated to optimize the end product (e.g. gene segment or gene of interest), particularly if the known end-product is shorter or longer.

In one embodiment, provided is a process for synthesizing a gene of interest, the process comprising the steps of:

a. Segmenting at least one nucleotide sequence comprising an open reading frame (ORF) encoding a gene of interest;

b. Factoring the segments from the at least one nucleotide sequence to obtain a first pool of oligonucleotides;

c. Assembling the first pool of oligonucleotides into gene segments;

i. Providing a second pool of oligonucleotides for assembling and amplifying the gene segments;

d. Purifying the assembled and amplified gene segments;

e. Heteroduplexing the purified gene segments in step d. to form mismatched base pairs;

i. Mismatch digesting the gene segments comprising mismatched base pairs to obtain digest fragments;

ii. Purifying the digest fragments to obtain error-free gene segments;

f. Amplifying the error-free gene segments;

i. Purifying the error-free gene segments of interest; and, g. Assembling the gene segments of interest into a gene of interest, thereby synthesizing the gene of interest.

Error Reduction

During gene synthesis errors present in designed oligonucleotides get integrated into the assembled products, and the proofreading mechanisms of high fidelity polymerases propagate errors present in the template strand to the new strand, thereby spreading errors onto both strands of double stranded molecules. Hence, according to the invention, one method to reduce these errors comprises distributing the errors by generating heteroduplex nucleic acid sequences and then using mismatch base pair repair to reduce the errors in these sequences. In generating a heteroduplex, the double stranded nucleic acid is denatured into single stranded molecules, and the temperature is slowly reduced to allow random pairing of complementary strands. Mismatches are created when one strand has an error and the other does not.

Accordingly, in one embodiment of the invention provided is a process for reducing base pair error rate in the chemical synthesis of a gene of interest, the process comprising the steps of:

a. obtaining a pool of assembled gene segments confirmed to contain mismatch errors;

b. denaturing the purified gene segments into single stranded nucleic acid sequences and allowing random pairing of complementary strands, wherein the paired complementary strands or gene segments comprise mismatched base pairs;

i. mismatch digesting the gene segments comprising mismatched base pairs to obtain digest fragments;

ii. purifying the digest fragments according to size to obtain error-free gene segments;

c. amplifying the error-free gene segments;

i. purifying the error-free gene segments of interest, thereby reducing base pair error rate in the chemical synthesis of a gene of interest.

In some embodiments, the process for reducing base pair error rate in the chemical synthesis of a gene of interest further comprises repeating steps a.-c. to further reduce base pair error rate.

In another embodiment, the process of error reduction further comprises confirming that the gene segments following the purification in steps b.-c. are of correct size and concentration. Methods for determining the correct size and concentration are readily available in the art, examples of which are further disclosed elsewhere herein.

Chemical synthesis of oligonucleotides has a relatively high error rate, which limits the size of genes that can be reliably synthesized. In one embodiment, gene segments in the pool of sequences that are to undergo error reduction according to the process of the invention are comprised of double stranded nucleic acid sequences and these comprise one or more sequence errors in the nucleic acid sequence. In some embodiments, a gene segment disclosed herein comprises DNA or cDNA. In some embodiments, the errors are mismatch base pair errors. In other embodiments, the mismatch base pair errors are introduced into the gene segment following the assembly of the gene segment in the gene synthesis process. As a result, the mismatch base pair errors propagate during assembly and amplification of the gene segment or gene of interest.

In some embodiments, the processes of the present disclosure comprise generating heteroduplexes of the synthesized gene fragments. In some embodiments, generating the heteroduplexes comprises the following steps an initial incubation at 95 ° C. for 10 minutes, followed by a temperature ramp of –2.0 ° C./second to 85° C., incubation at 85° C. for 1 minute, a temperature ramp of –0.3° C./second to 75° C., incubation at 75° C. for 1 minute, a temperature ramp of –0.3° C./second to 65° C., incubation at 65° C. for 1 minute, a temperature ramp of –0.3° C./second to 55° C., incubation at 55° C. for 1 minute, a temperature ramp of –0.3° C./second to 45° C., incubation at 45° C. for 1 minute, a temperature ramp of –0.3° C./second to 35° C., incubation at 35° C. for 1 minute, a temperature ramp of –0.3° C./second to 25° C., incubation at 25° C. for 1 minute, optionally followed by a 4 C hold. The person or ordinary skill will understand that the individual steps can be varied by time, temperature and ramp conditions to optimize heteroduplexing for a particular synthesized gene fragment.

In one embodiment, the processes of the present disclosure comprise the step of reducing error rates in the synthesis of a gene of interest. In another embodiment, the step of mismatch digesting comprises using an endonuclease. In a particular embodiment, the endonuclease used in the process of the invention is a T7 endonuclease I. T7 Endonuclease I (referred to herein as T7E1) recognizes and cleaves mismatched DNA, heteroduplex DNA, cruciform DNA, Holliday structures and/or junctions, as well as nicked double-stranded DNA. This enzyme has a preference for single stranded over double stranded DNA with cleavage occurring at the first, second or third phosphodiester bond that is 5' to the mismatch. This enzyme is also good at detecting insertions and deletions, which are the primary types of errors introduced on oligos used in the gene fragment synthesis process. T7E1 is also more specific than other endonucleases, i.e. has less random cleavage. T7E1 therefore provides superior specificity in cleaving DNA heteroduplexes generated by errors in the gene fragment synthesis methods of the disclosure.

In one embodiment, the mismatch digesting according to the process of the invention is carried out at about 42° C. In another embodiment, the mismatch digesting is carried out at 43° C., 41° C., 40° C., 39° C., 38° C., or 37° C. In another embodiment, the mismatch digesting is carried out at 42° C. While temperature is used, in an embodiment, to improve the mismatch digestion properties of T7E1, chemical agents which decrease base pairing efficiency, such as di-methyl sulfoxide (DMSO) and Betaine, may be used to produce similar results at lower temperatures.

In various embodiments of the present disclosure, error removal steps may also be implemented by executing processor-executable instructions. The invention thus includes software based instructions for performing mechanical functions associated with error removal processes, as well as other aspects of the invention.

In one embodiment, each purification step in the error reduction process comprises using gel excision or solid phase reversible immobilization (SPRI) to assess purity.

In one embodiment, the high-fidelity process of the invention is used to generate DNA with substantially reduced error rates for transcription and production of modified RNA molecules of interest. Accordingly, the present invention relates to a modified RNA molecule of interest produced by the process of the invention.

In another embodiment, provided is a process for reducing base pair error rate in the synthesis of a gene of interest, the process comprising the steps of:

a. obtaining a pool of assembled gene segments confirmed to contain mismatch errors;

b. heteroduplexing the gene segments to form mismatched base pairs;

i. mismatch digesting the gene segments comprising mismatched base pairs to obtain digest fragments;

ii. purifying the digest fragments to obtain error-free gene segments;

c. amplifying the error-free gene segments; and, i. purifying the error-free gene segments of interest, thereby reducing base pair error rates in the synthesis of a gene of interest.

Applications

Aspects of the invention may be useful for a range of applications involving the production and/or use of synthetic nucleic acids. As described herein, the invention provides methods for synthesizing synthetic nucleic acids. Some aspects of the invention relate to a gene synthesis platform using methods described herein.

In some embodiments, the assembly procedure may include several parallel and/or sequential reaction steps in which a plurality of different nucleic acids or oligonucleotides are synthesized and/or generated from a larger double stranded nucleic acid molecule, and are combined in order to be assembled and amplified (e.g., by PCA and PCR as described herein) to generate a longer nucleic acid product to be used for further assembly, cloning, or other applications.

The assembled nucleic acids produced by the process provided herein may be amplified in vitro (e.g., using PCR, ligase chain reaction (LCR), or any suitable amplification technique), amplified in vivo (e.g., via cloning into a suitable vector), isolated and/or purified. Nucleic acid amplification methods may also include, without limitation, polymerase chain reaction (PCR) (U.S. Pat. No. 5,219,727) and its variants such as in situ polymerase chain reaction (U.S. Pat.

No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers.

An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

In some embodiments, the process of the invention is used to generate modified RNA transcripts. In one embodiment, the RNA transcript is between 100 and 10,000 nucleotides in length. In other embodiments, the RNA transcript is between 600 and 10,000, or between 700 and 3,000 nucleotides in length. In another embodiment, the RNA transcript is a full length RNA transcript. In another embodiment, the RNA transcript includes chemically modified ribonucleotides. In an embodiment, the RNA transcript is the product of in vitro transcription using an amplified DNA template produced by the methods disclosed herein.

Many of the techniques described herein can be used together, applying suitable assembly techniques at one or more points to produce long nucleic acid molecules. For example, ligase-based assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agri-cultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e. using cell-free systems) or in vivo (i.e. expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexa-histidine (His[6]) Myc and HA, and other polypeptides with utility, such as GFP5 GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids. In certain embodiments, synthetic nucleic acids may be provided as libraries for screening in research and development (e.g., to identify potential therapeutic proteins or peptides, to identify potential protein targets for drug development, etc.) In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

In some embodiments, the assembled double stranded nucleic acid molecules (e.g.-gene segments, plasmids, PCR products, genes of interest) may be introduced into any number of cells including prokaryotic and eukaryotic cell.

As one skilled in the art would understand, many aspects of the invention are well suited for automation. Automated systems are often driven by software which may perform repetitive tasks, especially when integrated with hardware designed for micromanipulation of components and reagent flows. Thus, according to various embodiments described herein, methods of synthesizing and assembling nucleic acids may be implemented on a computing system. Further, according to various embodiments described herein, processor-executable instructions for assembling and synthesizing nucleic acids. Thus, in some aspects the invention includes non-transitory computer-readable storage media encoded with instructions, executable by a processor, for generating assembled nucleic acid molecules.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The following examples are presented in order to more fully illustrate the preferred embodiments of the invention. They should in no way be construed, however, as limiting the broad scope of the invention.

EXAMPLES

Example 1

Figure 2:
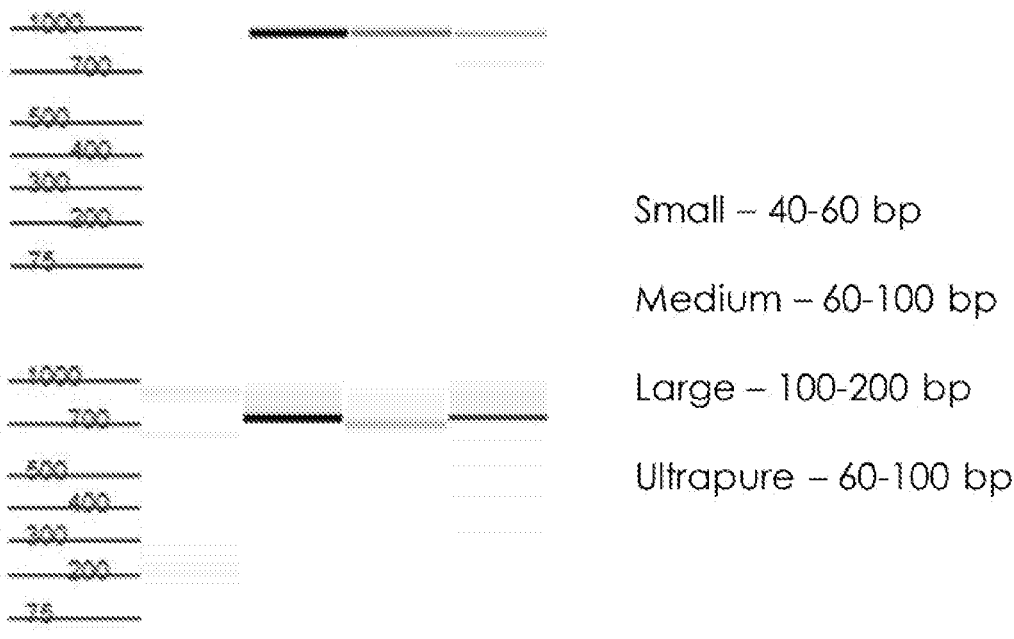
FIG. 2 illustrates a Sequence Segmentation. Two gene segments were factored into oligos of various lengths. The gene segments were then assembled and amplified from those oligos. Fragments, from left to right, are small (40-60 bp), medium (60-100 bp), large (100-200 bp) and ultrapure (60-100 bp). Top row: Bla; bottom row: Cat.
Figure 3B:
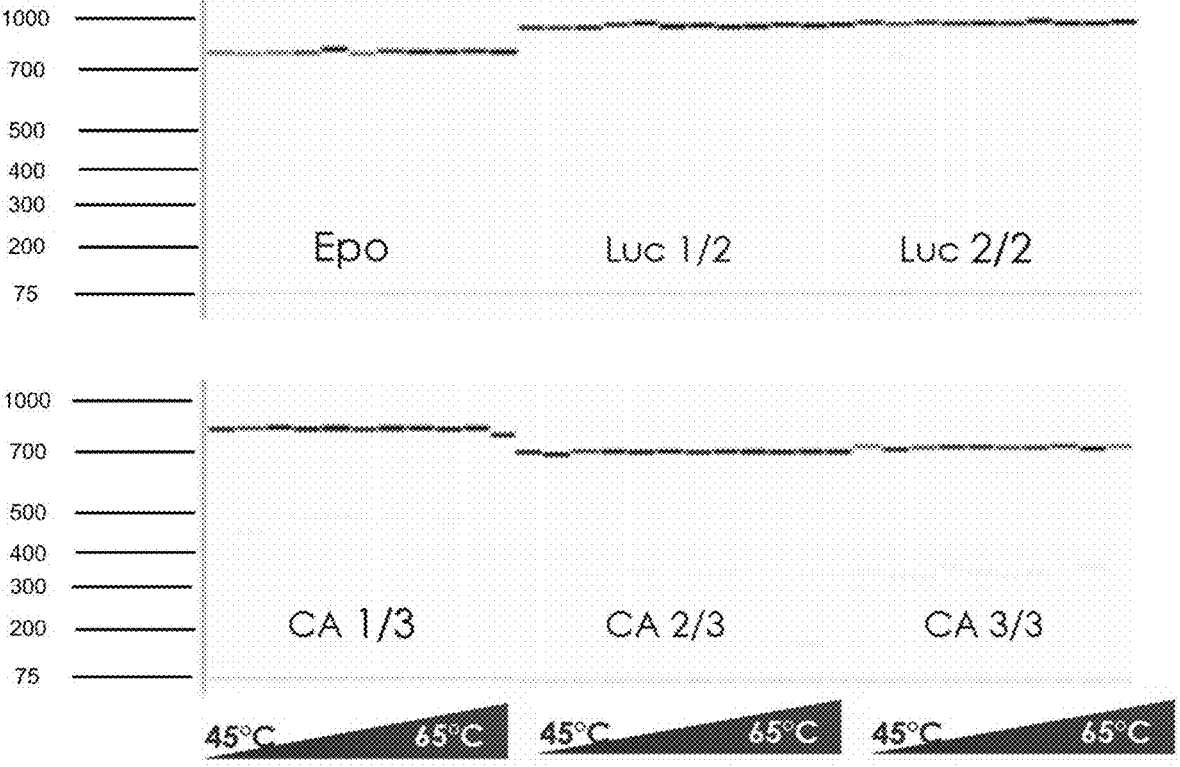
Figure 4A:
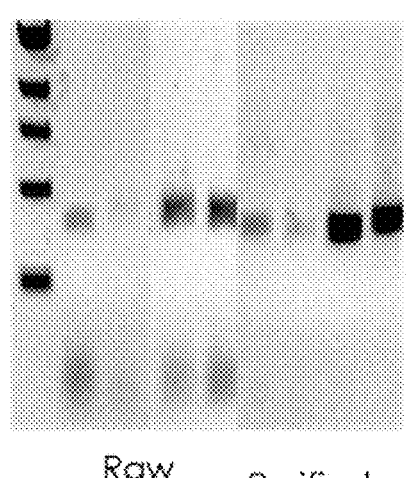
FIG. 4A-B illustrates purification at various gene synthesis steps.
Figure 4B:
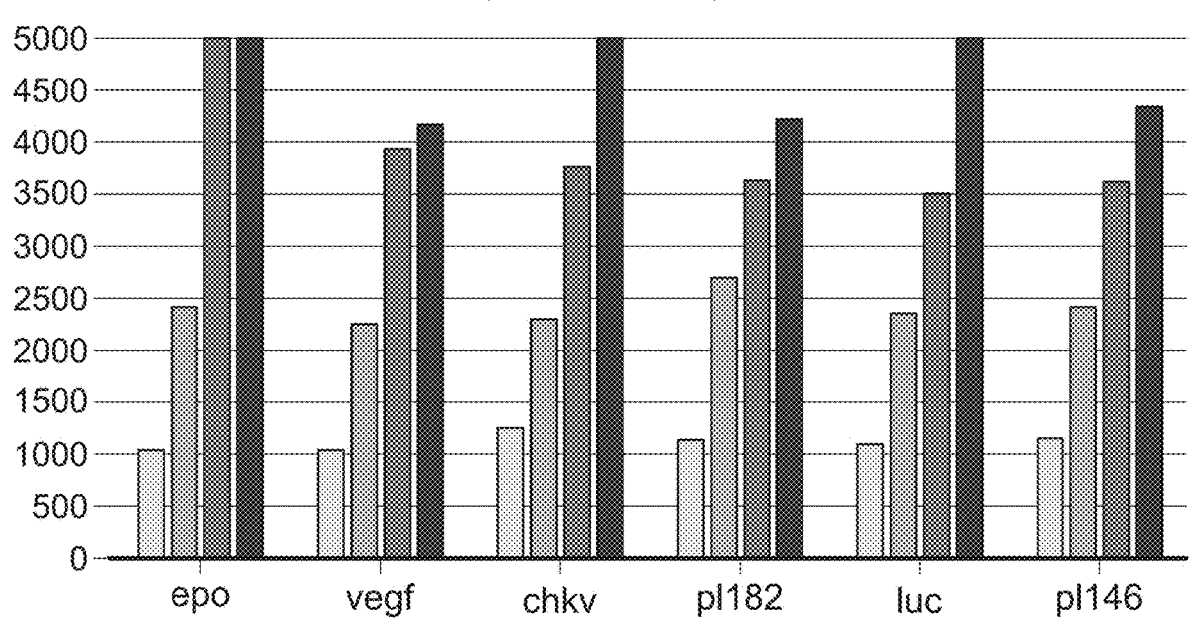

Rapid, High-Fidelity Method to Support Synthesis
of Genes for In Vitro Transcription of Modified
Messenger RNA Discussed herein below is a process for reducing sequence error rates in the chemical synthesis of a gene of interest.
1. Sequence Segmentation In the current iteration, sequences are sectioned into segments of <1000 base pairs (bp) with 30 bp overlaps between segments, and each segment further factored into oligos with length of 60 to 90 bases, overlaps between oligos of 20 bp, and a GC content of 48-52% in the overlap region. The overlaps between sections as well as between oligos are also designed to consider the "uniqueness" of the chosen overlap sequence within the sequence as a whole. These parameters could be changed as further optimization occurs. Testing included other oligo lengths, as seen in FIG. 2.
2. Oligo Assembly Oligo assembly into the full length segment is performed via polymerase chain assembly using an equimolar pool of the oligos. Briefly, oligos are ordered at a concentration of 10 uM each, and are pooled at an equimolar ratio. While multiple dilutions were tested and found to be acceptable, in the current iteration, that pool is diluted 10× into the polymerase chain assembly reaction. Multiple polymerases, annealing temperatures, and cycle numbers were evaluated and found to be acceptable, and the current iteration uses Q5 polymerase master mix with a thermocycling program of 90 seconds (s) at 95° C., 15 cycles of 15 s at 95° C., 15 s at 57° C., and 33 s at 72° C., and a final elongation of 90 s at 72° C.
3. Assembly Amplification To amplify the full length segment, the polymerase chain assembly reaction is diluted at 6% into a fresh PCR reaction with forward and reverse primer at 0.6 uM. Multiple dilutions, polymerases, annealing temperatures, and cycle numbers were evaluated and found to be acceptable (see FIG. 3), and the current iteration uses Q5 polymerase master mix with a thermocycling program of 90 seconds (s) at 95° C., 25 cycles of 15 s at 95° C., 15 s at 57° C., and 33 s at 72° C., and a final elongation of 90 s at 72° C.

4. Assembly Purification

Multiple methods of purification were evaluated, including column based methods, gel excision, and magnetic bead based methods (Solid Phase Reversible Immobilization/SPRI). Size-selective purifications, such as gel excision and size selective SPRI were shown to be superior in minimizing errors propagating to the final product. The current iteration adds an equal volume of bead mix (1 mg/ml beads in 1.5M NaCl, 15% PEG8000, 15 mM Tris-HCl, 1 mM EDTA) to the PCR reaction, which is washed two times with 70% Ethanol, and eluted with water.

5. Assembly Size Confirmation, and Quantitation

Multiple methods can be used to confirm that the oligos assembled into a segment of the correct size, including agarose gel electrophoresis, capillary electrophoresis, or other chromatographic methods. Likewise, concentration of the purified assembly can be determined by multiple methods, including optical density at 260 nm, gel densitometry, or fluorescent intercalating dyes. The current iteration uses capillary electrophoresis to verify the size and purity of the segment (similar to FIG. 3A), and optical density at 260 nm to determine concentration.

6. Heteroduplexing

As the errors from oligos will be integrated into the assembled products, and the proofreading mechanisms of high fidelity polymerases will propagate errors present in the template strand to the new strand, errors will be present on both strands of double stranded molecules. One method to distribute these errors is to use heat to denature the double stranded molecules into single stranded molecules, and slowly reduce temperature to allow random pairing of complementary strands. Mismatches are created when one strand has an error and the other does not. While multiple methods were tested and found to be acceptable for generating heteroduplexes, the current iteration uses DNA at 6.7 ng/ul in a final buffer consisting of 50 mM NaCl, 10 mM Tris-HCl, 10 mM MgCl$_2$, 1 mM DTT, and pH 7.9 with a program of 10 minutes at 95° C., followed by a temperature ramp decreasing at 0.3° C. per second to 25° C., with a 1 minute hold every 10° C.

7. Mismatch Digest

Figure 5A:
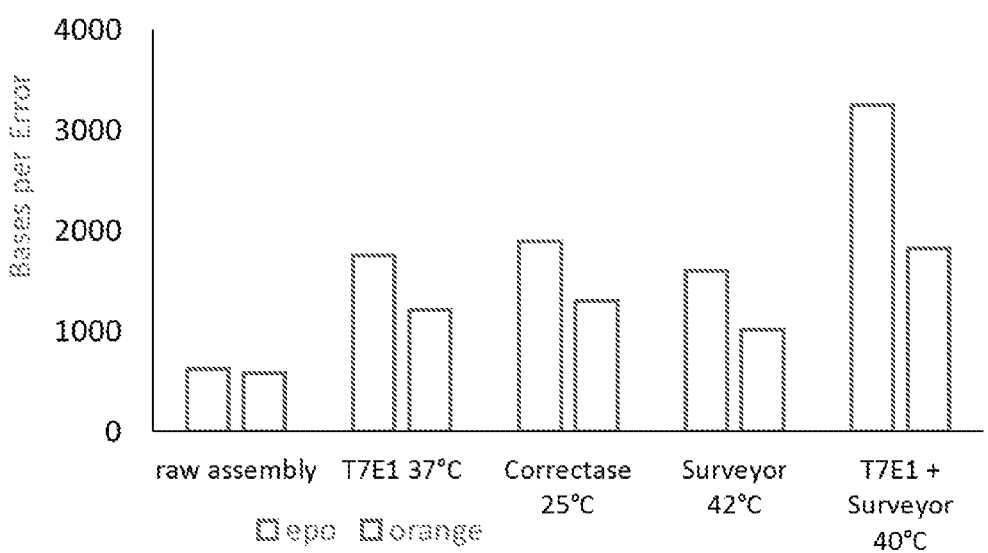
FIG. 5A-B illustrates mismatch digest enzyme comparison.
Figure 5B:
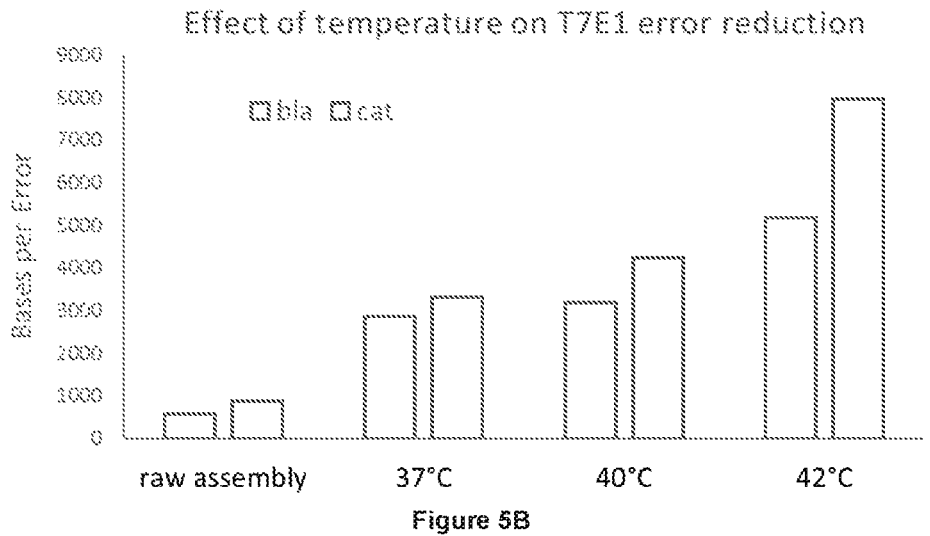
Figure 6:
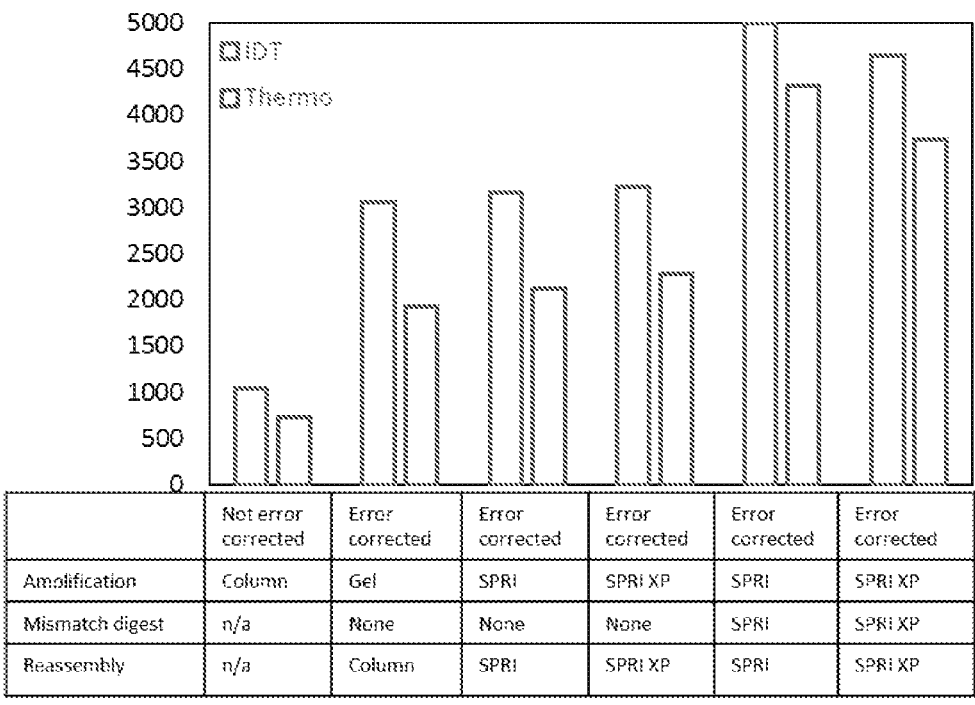
FIG. 6 illustrates mismatch digest purification. Oligo pools from two vendors were assembled, purified, and corrected as indicated. Two SPRI vendors were compared. While SPRI post amplification and reassembly is equivalent to gel purification post assembly and column cleanup post reassembly, adding a SPRI step post mismatch digest enhances the error reduction.

Multiple enzymes and enzyme combinations were tested for the ability to recognize and digest mismatches in heteroduplexed gene segments. While all were active to some degree, T7 Endonuclease I removed the most errors per round of heteroduplexing, mismatch digest, and reassembly. Furthermore, error reduction improved with increasing temperatures, despite the reported optimal activity at 37° C. (FIG. 5). The current iteration uses T7 Endonuclease I at a concentration of 1 U/ul heteroduplexed DNA from step 6, and the reaction is incubated for 30 minutes at 42° C.

8. Digest Purification

Multiple methods of purification were evaluated, including column based methods, gel excision, and magnetic bead based methods (Solid Phase Reversible Immobilization/SPRI). Size-selective purifications, such as gel excision and size selective SPRI were shown to be superior in minimizing errors propagating to the final product. The current iteration adds an equal volume of bead mix (1 mg/ml beads in 1.5M NaCl, 15% PEG8000, 15 mM Tris-HCl, 1 mM EDTA) to the PCR reaction, which is washed two times with 70% Ethanol, and eluted with water.

9. Reassembly

To reassemble the full length segment, the mismatch digest reaction is diluted at 6% into a fresh PCR reaction, with forward and reverse amplification primers at 0.6 uM. Multiple dilutions, polymerases, annealing temperatures, and cycle numbers were evaluated and found to be acceptable, and the current iteration uses Q5 polymerase master mix with a thermocycling program of 90 seconds (s) at 95° C., 25 cycles of 15 s at 95° C., 15 s at 57° C., and 33 s at 72° C., and a final elongation of 90 s at 72° C.

10. Reassembly Purification

Multiple methods of purification were evaluated, including column based methods, gel excision, and magnetic bead based methods (Solid Phase Reversible Immobilization/SPRI). Size-selective purifications, such as gel excision and size selective SPRI were shown to be superior in minimizing errors propagating to the final product. The current iteration adds two volumes of bead mix (1 mg/ml beads in 1.5M NaCl, 15% PEG8000, 15 mM Tris-HCl, 1 mM EDTA) to the PCR reaction, which is washed two times with 70% Ethanol, and eluted with water.

11. Reassembly Size Confirmation, and Quantitation

Multiple methods can be used to confirm that the digested heteroduplexes reassembled into a segment of the correct size, including agarose gel electrophoresis, capillary electrophoresis, or other chromatographic methods. Likewise, concentration of the purified reassembly can be determined by multiple methods, including optical density at 260 nm, gel densitometry, or fluorescent intercalating dyes. The current iteration uses capillary electrophoresis to verify the size and purity of the segment (similar to FIG. 3A), and optical density at 260 nm to determine concentration.

Having described embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

Example 2

Heteroduplex Based Error Correction is Highly Effective at Reducing Errors in Assembled Gene Fragments Empty manufacturing plasmid was digested with SapI enzyme for 16 hours, followed by de-phosphorylation with CIP (NEB) and column purification.

Gene synthesis was performed using seed oligos purchased from IDT to assemble the EPO gene. All seed oligos and primers, used for assembly and amplification of gene fragments, respectively, were at a concentration of 3.3 μM and were pooled together in equal volumes to create a seed oligo pool. 3 μL of this oligo pool was used to assemble EPO gene fragments in a 50 μL total-volume PCR reaction using Q5 DNA polymerase (NEB).

The assembly PCR reaction was assembled as shown in table 1 below:

| Raw materials | Volume per reaction (in µL) |
|---|---|
| Water | 22 |
| 2X Q5 mastermix | 25 |
| Oligos | 3 |
| Total volume | 50 |

The assembly PCR reaction was performed as shown in table 2 below:

| Step # | Temperature (° C.) | Time (seconds) |
|---|---|---|
| 1 | 98 | 120 |
| 2 | 98 | 20 |
| 3 | 57 | 15 |
| 4 | 72 | 60 |
| Repeat steps 2-4, 15 cycles | | |
| 5 | 72 | 300 |
| 6 | 4 | ∞ |

Following assembly PCR, the assembly PCR product was diluted 3-fold in water. 4.5 µL of diluted Assembly PCR product was used as template for the amplification PCR reaction. In a total volume of 75 µL, 13.5 µL of pooled primers were used to amplify the assembled gene fragments with PCR reaction and cycling conditions shown in tables 3 and 4 below.

TABLE 3

| Amplification PCR composition | |
|---|---|
| Raw materials | Volume per reaction (in µL) |
| Water | 19.5 |
| 2X Q5 mastermix | 37.5 |
| Pooled primers | 13.5 |
| 1:3 diluted assembly PCR product | 4.5 |

TABLE 4

| Amplification PCR composition | | |
|---|---|---|
| Step # | Temperature (° C.) | Time (seconds) |
| 1 | 98 | 120 |
| 2 | 98 | 20 |
| 3 | 57 | 15 |
| 4 | 72 | 60 |
| Repeat steps 2-4, 25 cycles | | |
| 5 | | 300 |
| 6 | | ∞ |

Half of the amplified PCR product was column purified and eluted into water. This purified DNA was then normalized to 50 ng/µL. 18 µL of this 50 ng/µL DNA was aliquoted into a PCR tube, and 2 µL of 10× NEB buffer 2 was added. Heteroduplexing (cycling method shown below in Table 5) was performed in a thermocycler to generate mis-matches.

TABLE 5

| Heteroduplex protocol. | | |
|---|---|---|
| Temperature | Time | Temperature ramp |
| 95° C. | 10 minutes | |
| 95° C. to 85° C. | | (−2.0° C./second) |
| 85° C. | 1 minute | |
| 85° C. to 75° C. | | (−0.3° C./second) |
| 75° C. | 1 minute | |
| 75° C. to 65° C. | | (−0.3° C./second) |
| 65° C. | 1 minute | |
| 65° C. to 55° C. | | (−0.3° C./second) |
| 55° C. | 1 minute | |
| 55° C. to 45° C. | | (−0.3° C./second) |
| 45° C. | 1 minute | |
| 45° C. to 35° C. | | (−0.3° C./second) |
| 35° C. | 1 minute | |
| 35° C. to 25° C. | | (−0.3° C./second) |
| 25° C. | 1 minute | |
| 4° C. | Hold ∞ | |

Following heteroduplexing, 2 µL of T7 endonuclease I (from NEB, 10 U/µL) was added and gently mixed, followed by incubation @42° C. for 45 minutes.

Figure 7:
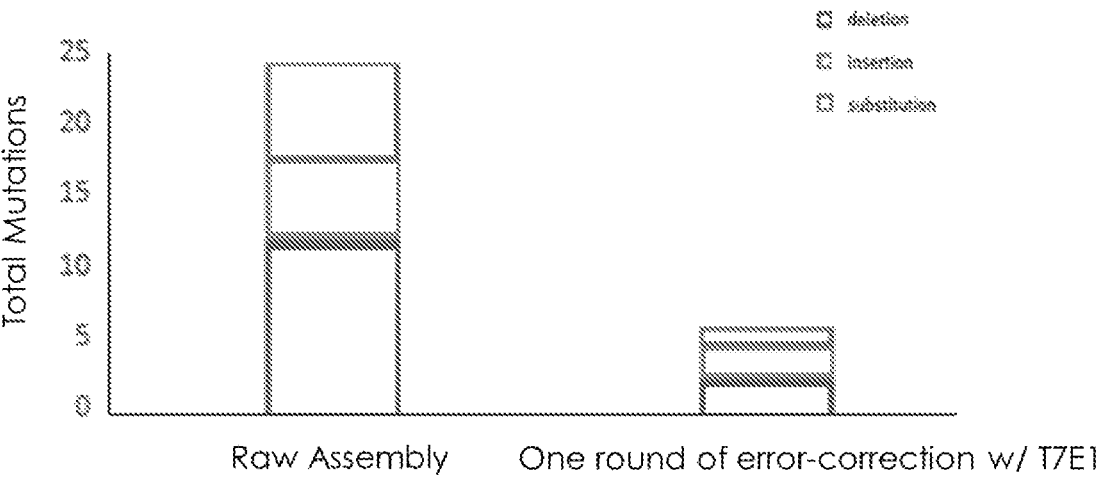
FIG. 7 illustrates the effectiveness of the T7E1 based error correction. Gene synthesis was performed using seed oligos to assemble and amplify the EPO gene. Gene fragments were either cloned into linearized plasmid backbone using Gibson assembly (left), or underwent heteroduplex based error correction prior to cloning (right). Heteroduplexing was performed in a thermocycler to generate mis-matches. Following cloning, plasmid clones isolated, mini-prepped and Sanger sequenced with full coverage of gene-fragment. Error rates were calculated as total number of errors normalized by total DNA basepairs sequenced. The bottom bar indicates deletions, the middle bar indicates insertions, and the top bar indicates basepair substitutions.

All PCR products (corrected and uncorrected) were gel-purified and cloned into linearized plasmid DNA backbone using Gibson assembly (100 ng backbone+50 ng gene fragment). 2 µL of Gibson assembly reaction was transformed into NEB Stable and plated onto LB+50 µg/ml kanamycin sulfate agar plates. Plates were incubated for 16 hours at 30° C. Following incubation, colonies were picked into 96-deep well plates (24 clones) containing 1.5 mL LB+50 µg/mL kanamycin and shaken overnight at 37° C., 250 rpm. Plasmid clones were mini-prepped and sent out for Sanger sequencing with complete coverage of gene-fragment. Error rates were calculated as total number of errors normalized by total DNA basepairs sequenced, and are shown in FIG. 7.

Figure 8:
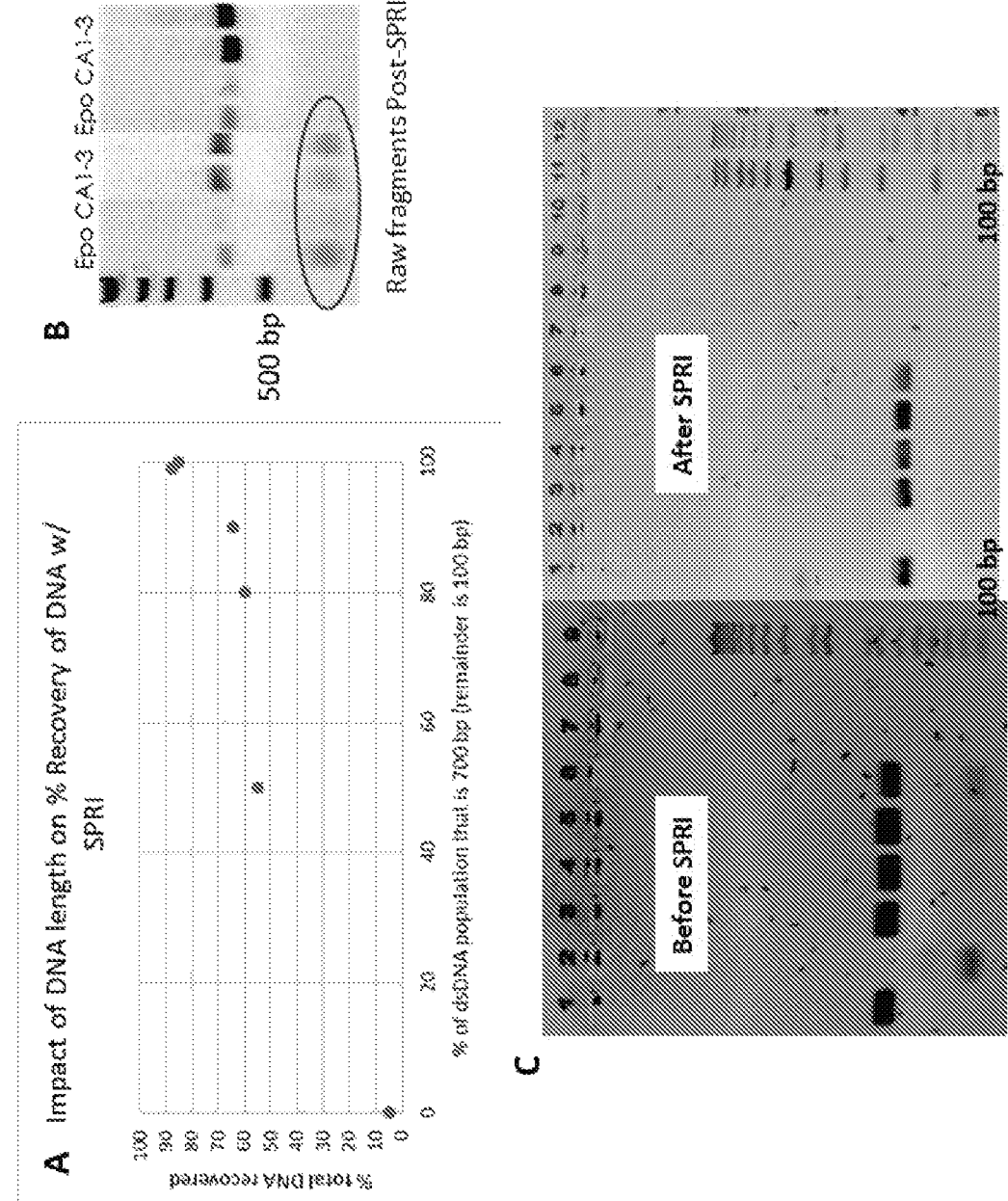
FIG. 8A-C illustrates the size-selective purification of gene fragments using solid phase reversible immobilization (SPRI) beads.
Figure 9:
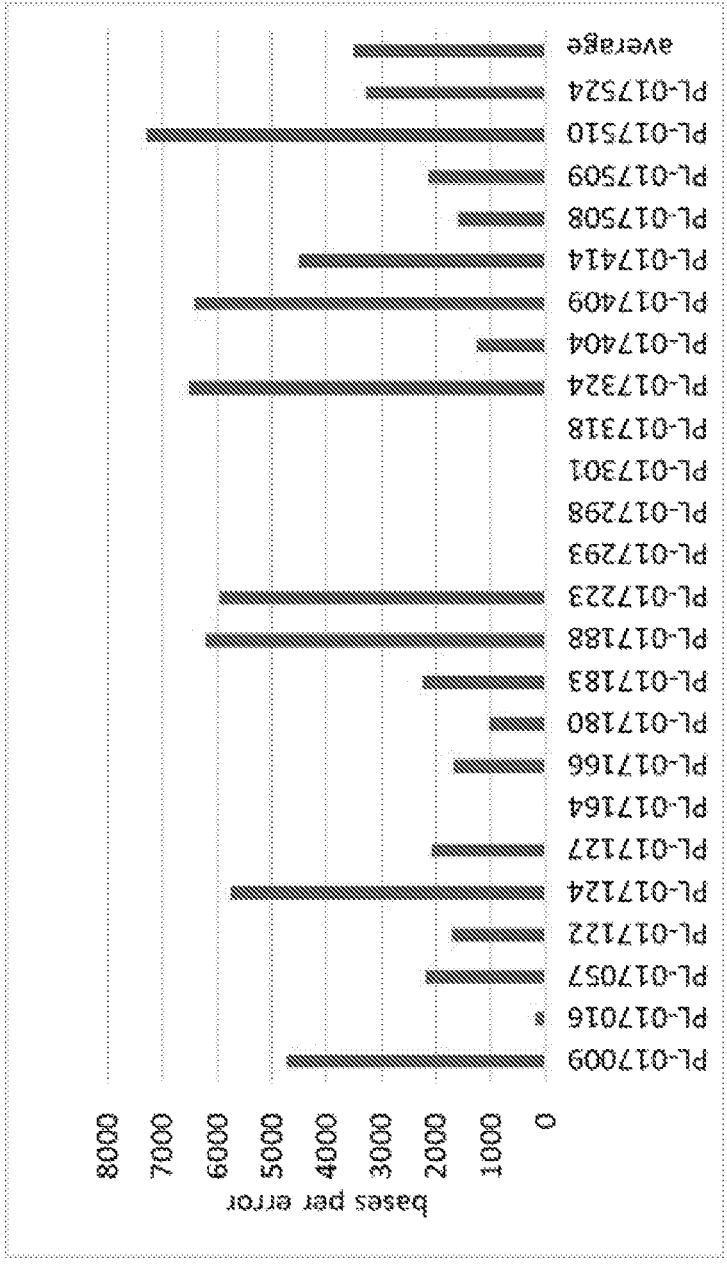
FIG. 9 illustrates the error rates in 24 gene fragments that were assembled, amplified and error corrected using the methods of the disclosure. 24 plasmids were constructed using Gibson assembly with plasmid backbone and a unique gene fragment constructed using the automated gene synthesis methods of the disclosure. 12 colonies per plasmid were picked into 96-deep well plates cultured, mini-prepped and Sanger sequenced with complete coverage of the gene fragment. Error rates were calculated as total number of colonies normalized by total DNA basepairs sequenced.

FIG. 9 shows an additional example of error rates in gene fragments that were assembled and error corrected using these methods. 24 plasmid constructs were constructed using Gibson assembly of a plasmid backbone and a unique gene fragment constructed using the automated gene synthesis method. All gene fragments were assembled, amplified, and error-corrected using methods described in FIG. 7 and FIG. 8A. Gibson assembly reactions were transformed into NEB Stable cells and plated onto LB+50 µg/mL kanamycin sulfate and incubated overnight at 30° C. Following incubation, 12 colonies per plasmid were picked into 96-deep well plates containing 1.5 mL LB+50 µg/mL kanamycin sulfate and shaken overnight @37° C., 250 rpm. Plasmid clones were mini-prepped and Sanger sequenced with complete coverage of each gene fragment. Error rates were calculated as total number of colonies normalized by total DNA basepairs sequenced (FIG. 9). Surprisingly, 4 gene fragments show no errors whatsoever (PL-017293, PL-017298, PL-017391 and PL-017318). The remaining gene fragments show an average error rate approximately 1 error for every 4,000 basepairs, with some gene fragments having error rates as low as 1 error every 7,000 basepairs.

Example 3

Gene Fragments can be Effectively Purified and Size Separated Using SPRI

As shown in FIG. 8, gene fragments synthesized using the methods disclosed herein can be purified using SPRI beads and separated from smaller DNA fragments in reaction mixture such as oligos or short byproducts of the methods. This allows for superior speed compared to gel-extraction based purification methods, and is compatible with a variety of automatic gene synthesis platforms.

PCR products of 100 bp and 700 bp in length were generated using the primers pairs:

```
5seq:
                                    (SEQ ID NO: 1)
(5'-TCAAGCTTTTGGACCCTCGTACAG-3')
and KS476
                                    (SEQ ID NO: 2)
(5'TCTTCCATGGTGGCTCTTATATTTCTTC);
``` as well as

5seq (5' TCAAGCTTTTGGACCCTCGTACAG) (SEQ ID NO: 1) and

KS482 (5'GTGCTACCCGAGGAATTCATAATCAG) (SEQ ID NO: 3), respectively, with Q5 DNA polymerase and PL-007984 as template DNA. PCR product was column purified and eluted in water. Six tubes containing various ratios of 100 bp:700 bp product (by mass) were prepared in a total volume of 50 µL. Each sample was then purified using SPRI, eluted in water, and run on a fragment analyzer to quantify % of total purified DNA that is 700 bp in length. SPRI was performed using Sera-mag beads (20 µL of bead solution per ml SPRI buffer) that were washed once in water and re-suspended in buffer D (20% PEG8000, 2 M salt, 10 mM Tris pH 8, 1 mM EDTA). DNA was bound to the SPRI beads in buffer D by adding 50 µL of SPRI+Buffer to 50 µL of DNA. After a 2-minute incubation at room temperature, the SPRI beads were brought to bottom of the tubes with a magnet and the supernatant was removed. Tubes were removed from the magnet, and washed in 100 µL 70% ethanol. After 2 washes, the supernatant was removed and the SPRI beads were allowed to dry at room temperature for 10 minutes. The DNA was eluted with 50 µL water and incubated for 2 minutes at room temperature before being re-magnetized and purified DNA in water was removed and transferred into clean tubes. The results are shown in FIG. 8A.

In FIG. 8B, EPO, CA1, CA2 and CA3 fragments were generated from oligos by assembly and amplification PCR as described in methods for FIG. 7 (Example 2). Half of each fragment was purified by SPRI as described in methods for FIG. 8A above. Samples of each fragment (before and after SPRI purification) were run on 1% agarose gels to visualize presence and/or absences of smaller fragments (oligos, primers, short byproducts).

The CA1 DNA fragment was generated from oligos by assembly and amplification PCR as described in methods for FIG. 7 (Example 2). Each fragment was purified by SPRI as described in the methods above for FIG. 8A. Samples of each fragment (before and after SPRI purification) were run on 1% agarose gels to visualize presence and/or absences of smaller fragments (oligos, primers, short byproducts), and the results are shown in FIG. 8C.

Example 4

Rapid Synthesis of a Panel of 84 Mutants in an Enzyme

One application of the methods of the disclosure is the rapid and cheap synthesis of panels of mutants. In this example, a 550 bp gene fragment was targeted for mutagenesis. The region targeted for mutagenesis was covered by three overlapping oligos (FIG. 10A), so that 9 out of 12 oligos used to tile the gene fragment could be used in the synthesis of all mutant clones. This resulted in a drastically reduced cost per mutant when compared to the cost de novo synthesis of each mutant, for example as a gene block.

Figure 10:
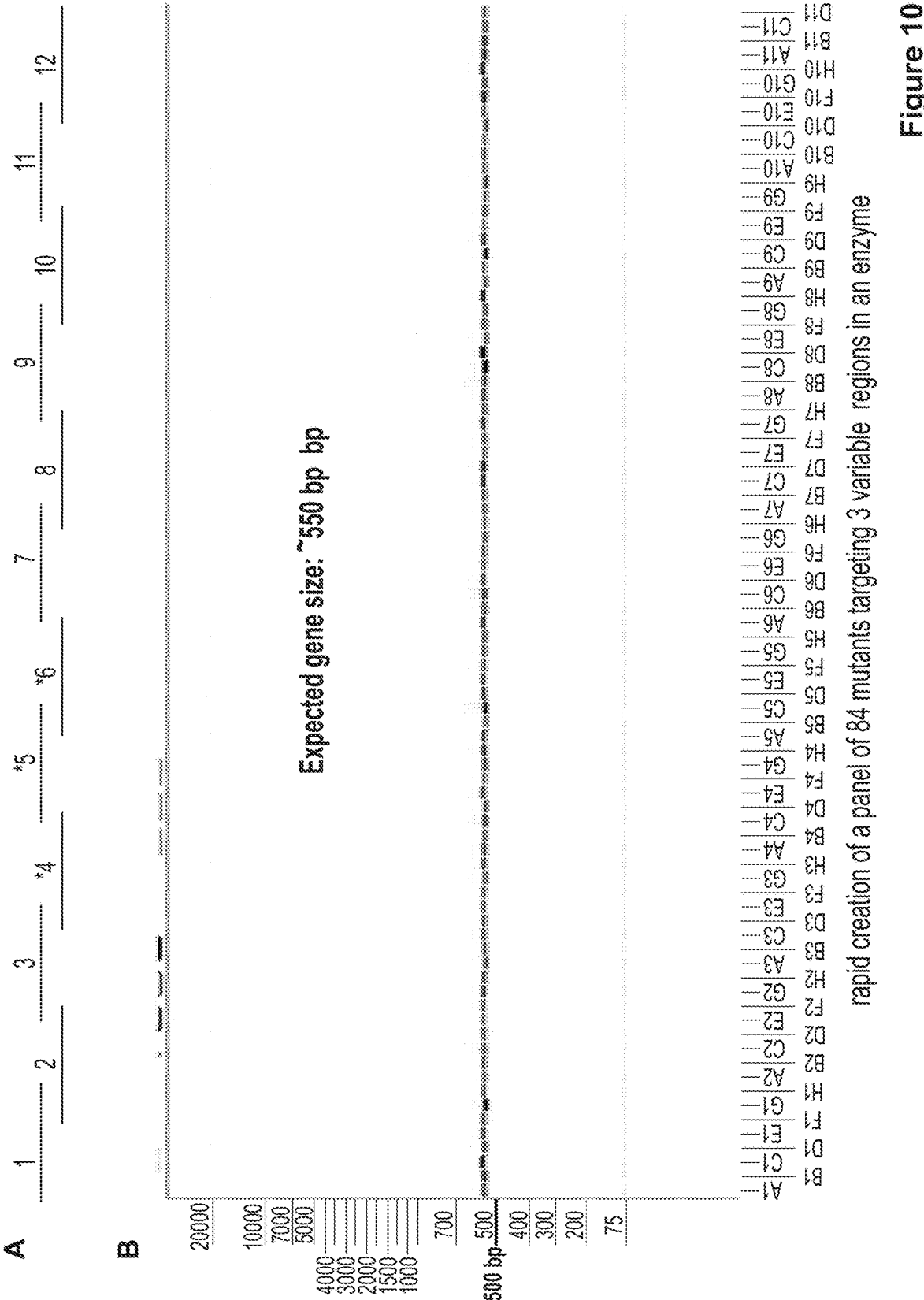
FIG. 10A-B illustrates how the methods of the disclosure can be used to rapidly assemble a large panel of 84 mutants.

Each gene fragment variant required 12 assembly oligos for synthesis. However, 9 of the 12 oligos are identical amongst all desired variants. A universal pool was generated in which oligos 1-3 and 7-12 were mixed together in equal volumes (all at a concentration of 3.3 µM). This universal pool was aliquoted into a 96-well PCR plate (84 wells total, 50 µL per well). The variable oligos for regions 4, 5 and 6 were ordered in pre-arrayed 96 well plates at a concentration of 3.3 µM. To create the final oligo pool used to assemble each desired variant, 3 µL of each well of each of the 3 PCR plates containing variant oligos were 'stamped' into the plate containing the universal pools. Following oligo pooling, the gene fragments were assembled and amplified using the methods described in FIG. 7 (example 2). As the size of the gene fragment was only 550 basepairs, no heteroduplex-based error correcting was performed. Gene fragment sizing was performed by running samples of each gene fragment on a fragment analyzer. All 84 variant assemblies produced gene fragments of the expected size (FIG. 10B).

What is claimed is:

1. A process for reducing base pair error rate during the synthesis of a gene of interest or a fragment thereof, the process comprising the steps of:

a) obtaining a pool of assembled gene segments that contain mismatched errors, wherein the pool of assembled gene segments form the gene of interest or the fragment thereof;

b) selecting error-less gene segments from the pool of assembled gene segments, comprising:

i) denaturing the pool of assembled gene segments into single stranded nucleic acid sequences and forming the paired gene segments by random pairing complementary strands of the single stranded nucleic acid sequences, wherein some of the paired gene segments comprise mismatched base pairs;

ii) generating a digest mixture containing error-less gene segments by mismatch digesting the paired gene segments with a T7 endonuclease I at 42° C.;

iii) obtaining error-less gene segments by purifying the error-less gene segments from the digest mixture according to sizes of the error-less gene segments; and c) producing amplified error-less gene segments by amplifying the error-less gene segments using a Q5 DNA polymerase;

thereby reducing base pair error rate during the synthesis of the gene of interest or the fragment thereof, wherein the error rate of each of the amplified error-less gene segments is less than about 1 error per 4,000 base pairs synthesized.

2. The process of claim 1, further comprising repeating steps a) through c).

3. The process of claim 1, wherein the pool of assembled gene segments comprise one or more sequence errors in one or more nucleic acid sequences in the pool of assembled gene segments.

4. The process of claim 1, wherein the gene of interest comprises a DNA sequence or a complementary DNA sequence from a cDNA.

5. The process of claim 1, wherein the mismatched errors are introduced into the paired gene segment by said random pairing complementary strands of the single stranded nucleic acid sequences.

6. The process of claim 1, further comprising a step for determining whether the error-less gene segments have correct sizes and whether the sizes of the error-less gene segments match the size of the gene of interest or the fragment thereof.

7. The process of claim 1, wherein step c) is performed using polymerase chain reaction (PCR).

8. The process of claim 1, wherein the assembled gene segments comprise at least one exon.

9. The process of claim 1, wherein step a) comprises:

i) obtaining a first pool of oligonucleotides by performing at least one segmenting step on at least one nucleotide sequence comprising an open reading frame (ORF) encoding the gene of interest or the fragment thereof;

ii) assembling and amplifying gene segments using the first pool of oligonucleotides and a second pool of oligonucleotides; and iii purifying the assembled and amplified gene segments produced in ii) of step a), thereby obtaining the pool of assembled gene segments.

10. The process of claim 9, wherein the at least one segmenting step produces gene segments with sizes up to 2000 base pairs comprising about 15-50 base pair overlap regions among the gene segments.

11. The process of claim 10, wherein the overlap regions comprise a GC content of about 40-60%.

12. The process of claim 9, wherein the first pool of oligonucleotides and the second pool of oligonucleotides are in an equimolar ratio.

13. The process of claim 12, wherein at least one oligonucleotide from the second pool of oligonucleotides is at least partially complementary to at least one oligonucleotide from the first pool of oligonucleotides.

14. The process of claim 12, wherein said assembling and amplifying gene segments comprises assembling the gene segments using a polymerase chain assembly, wherein the second pool of oligonucleotides is assembled with the first pool of oligonucleotides by the polymerase chain assembly to form the gene segments, and wherein a polymerase chain reaction (PCR) is used to amplify the gene segments.

15. The process of claim 9, wherein each oligonucleotide in the first pool of oligonucleotides is about 60 to 100 bases in length, and wherein each oligonucleotide in the first pool of oligonucleotides has an overlap region of about 20-50 base pairs.

16. The process of claim 1, wherein said purifying the error-less gene segments from the digest mixture is carried out by running the digest mixture on a gel using gel electrophoresis and recovering the error-less gene segments from the gel by gel excision after the gel electrophoresis or solid phase reversible immobilization (SPRI).

17. The method of claim 16, wherein the SPRI uses a buffer comprising 20% PEG8000, 2 M salt, 10 mM Tris pH 8 and 1 mM EDTA.

18. The process of claim 1, wherein the gene of interest or the fragment thereof comprises at least one exon sequence or at least one intron sequence.

19. The process of claim 1, wherein step b) comprises performing a heat denaturation reaction on the pool of assembled gene segments and slowly reducing the temperature of the heat denaturation reaction to promote said random pairing complementary strands of the single stranded nucleic acid sequences.

20. The process of claim 1, further comprising d) purifying the amplified error-less gene segments after step c).

21. The process of claim 1, further comprising e) assembling the amplified error-less gene segments into the gene of interest or the fragment thereof.

22. A process for reducing base pair error rate during the synthesis of a gene of interest or a fragment thereof, the process comprising the steps of:

a) obtaining a pool of assembled gene segments that contain mismatched errors, wherein the assembled gene segments form the gene of interest or the fragment thereof, b) selecting error-less gene segments from the pool of assembled gene segments, comprising:

i) denaturing the pool of assembled gene segments into single stranded nucleic acid sequences and forming the paired gene segments by random pairing complementary strands of the single stranded nucleic acid sequences, wherein some of the paired gene segments comprise mismatched base pairs;

ii) generating a digest mixture containing error-less gene segments by mismatch digesting the paired gene segments with a T7 endonuclease I at 42° C.;

iii) obtaining error-less gene segments by purifying the error-less gene segments from the digest mixture according to sizes of the error-less gene segments; and c) producing amplified error-less gene segments by amplifying the error-less gene segments using a high fidelity polymerase with proofreading activity, wherein the high fidelity polymerase with proofreading activity comprises a Q5 DNA polymerase, a Herculase DNA polymerase or a Phusion DNA polymerase, thereby reducing base pair error rate during the synthesis of the gene of interest or the fragment thereof, wherein the error rate of each of the amplified error-less gene segments is less than about 1 error per 4,000 base pairs.

23. The process of claim 22, comprising repeating steps a) through c).

24. The process of claim 22, wherein step a) comprises:

i) obtaining a first pool of oligonucleotides by performing at least one segmenting step on at least one nucleotide sequence comprising an open reading frame (ORF) encoding the gene of interest or the fragment thereof;

ii) assembling and amplifying gene segments using the first pool of oligonucleotides and a second pool of oligonucleotides; and iii) purifying the assembled and amplified gene segments produced in ii) of step a) thereby obtaining the pool of assembled gene segments.

25. The process of claim 24, wherein each oligonucleotide in the first pool of oligonucleotides is about 60 to 100 bases in length, and wherein each oligonucleotide in the first pool of oligonucleotides has an overlap region of about 20-50 base pairs.

26. The process of claim 24, wherein the at least one segmenting step produces gene segments with sizes up to 2000 base pairs comprising about 15-50 base pair overlap regions among the gene segments.

27. The process of claim 22, step b) comprises performing a heat denaturation reaction on the pool of assembled gene segments and slowly reducing the temperature of the heat denaturation reaction to promote said random pairing complementary strands of the single stranded nucleic acid sequences.

* * * * *